US010752677B2

(12) United States Patent
D'Acquisto et al.

(10) Patent No.: US 10,752,677 B2
(45) Date of Patent: Aug. 25, 2020

(54) METHODS OF TREATING OBSESSIVE COMPULSIVE DISORDER (OCD) OR ANXIETY USING AN ANTIBODY THAT BINDS TO ANNEXIN-1

(71) Applicant: Queen Mary & Westfield College, Univ. of London, London (GB)

(72) Inventors: Fulvio D'Acquisto, London (GB); Mauro Perretti, London (GB)

(73) Assignee: Queen Mary & Westfield College, University of London, London (GB)

( * ) Notice: Subject to any disclaimer, the term of this patent is extended or adjusted under 35 U.S.C. 154(b) by 0 days.

(21) Appl. No.: 14/365,311

(22) PCT Filed: Dec. 14, 2012

(86) PCT No.: PCT/GB2012/000906
§ 371 (c)(1),
(2) Date: Jun. 13, 2014

(87) PCT Pub. No.: WO2013/088111
PCT Pub. Date: Jun. 20, 2013

(65) Prior Publication Data
US 2015/0004164 A1    Jan. 1, 2015

(30) Foreign Application Priority Data
Dec. 14, 2011  (GB) .................... 1121564.7

(51) Int. Cl.
*A61K 39/395*  (2006.01)
*C07K 16/18*  (2006.01)
*A61K 39/00*  (2006.01)

(52) U.S. Cl.
CPC .......... *C07K 16/18* (2013.01); *A61K 39/3955* (2013.01); *A61K 2039/505* (2013.01); *C07K 2317/14* (2013.01); *C07K 2317/24* (2013.01); *C07K 2317/565* (2013.01); *C07K 2317/569* (2013.01)

(58) Field of Classification Search
None
See application file for complete search history.

(56) References Cited

U.S. PATENT DOCUMENTS

| | | | |
|---|---|---|---|
| 5,051,364 A | 9/1991 | Isacke et al. | |
| 5,162,311 A * | 11/1992 | Herrling | C07F 9/4056 514/110 |
| 5,565,338 A | 10/1996 | Ishizaka | |
| 5,567,440 A * | 10/1996 | Hubbell | A61K 9/5031 424/484 |
| 2005/0113297 A1 | 5/2005 | Francois et al. | |
| 2006/0024315 A1 | 2/2006 | Schnitzer et al. | |

FOREIGN PATENT DOCUMENTS

| | | | |
|---|---|---|---|
| CN | 1726395 A | | 12/2013 |
| WO | 03057715 | | 7/2003 |
| WO | 2005027965 | | 3/2005 |
| WO | 2005117848 | | 12/2005 |
| WO | 2007139813 | | 12/2007 |
| WO | 2010064012 | | 6/2010 |
| WO | 2011154705 | | 12/2011 |
| WO | WO/2013/088110 | * | 6/2013 |
| WO | 2018146230 | | 8/2018 |

OTHER PUBLICATIONS

Gao et al. Reduced Fear Memory and Anxiety-like Behavior in Mice Lacking Formylpeptide Receptor 1. Behav Genet. 41(5): 724-733, 2011.*
Alonso et al. Animal models of obsessive-compulsive disorder: utility and limitations. Neuropsychiatric Disease and Treatment 2015:11 1939-1955.*
D'Angelo1 et al., Many routes to an antibody heavy-chain cDr3: necessary, Yet insufficient, for specific binding. Front. Immunol., Mar. 8, 2018, 1D'Angelo1 et al., Front. Immunol., Mar. 8, 2018, Jan. 13, 2013 (Year: 2018).*
Tang et al., Genetic immunization is a simple method fro eliciting an immune repsonse, Nature 1992 356:152-154.
Barderas et al., Affinity maturation of antibodies assisted by in sillico modeling, PNAS 2008 105(26):9029-9034.
Brown et al. Tolerance of single, but not multiple, amino acid replacements in antibody VH CDR 2: a means of minimizing B cell wastage from somatic hypermutation? J. Immuno. May 1996, 3285-91.
Buckingham et al., Lipcortin 1: a second messenger of glucocorticoid action in the hypothalamo-pituitary-adrenocortical axis, Mol Med Today 1997 3(7):296-302.
Buckingham, Stress and the neuroendocrine-immune axis: the pivotal role of glucocorticoids and lipocortin 1, British J Pharm 1996 1-19.
Cai et al. Preparation and identification of monoclonal antibody against annexin I. Zhongliu 2006 26(11): 979-983, English Abstract only.
Cui et al., Overexpression of annexin A1 induced by terephthalic acid calculi in rat bladder cancer, Proteomics 2007 7(22):4192-4202.
D'Acquisto et al., Annexin-1 modulates T-cell activation and differentiation, Blood 2007 109(3):1095-1102.
D'Acquisto et al., Annexin-A1: a pivotal regulator of the innate and adaptive immune systems, British J Pharm 2008 155(2):152-169.
D'Acquisto et al., Glucocorticoid treatment inhibits annexin-1 expression in rheumatoid arthritis CD4+ T cells, Rheumatology 2008 47(5):636-639.

(Continued)

Primary Examiner — Maher M Haddad
(74) Attorney, Agent, or Firm — Stradley Ronon Stevens & Young, LLP

(57) ABSTRACT

The present invention provides a specific binding molecule that binds to Annexin-1 (Anx-A1) for use in the treatment of obsessive compulsive disorder (OCD) or a disease related to OCD. The invention also provides a pharmaceutical composition comprising a specific binding molecule of the invention for use in the treatment of obsessive compulsive disorder (OCD) or a disease related to OCD.

8 Claims, 15 Drawing Sheets

Specification includes a Sequence Listing.

(56) References Cited

OTHER PUBLICATIONS

D'Acquisto et al., Impaired T cells activation and increased Th2 lineage commitment in Annexin-1-deficient T cells, Eur J Immunol 2007 37(11):3131-3142.
D'Acquisto, From the bench to the pipline: testing the immunosuppressive potential of novel therapies targeting annexin A1, Immunology 2010 131:159.
D'Acquisto, On the adaptive nature of annexin-A1, Curr Opin Pharmacol 2009 9(4):521-8.
Dijkstra et al., "Multiple sclerosis: some possible therapeutic opportunities", TIPS Reviews, 1993, 14:124-129.
Falini et al., Simple diagnostic assay for hairy cell leukaemia by immunocytochemical detection of annexin A1 (ANXA1), Lancet 2004 363(9424):1869-70.
Flower et al., Lipocortin-1: cellular mechanisms and clinical relevance, Trends Pharmacol Sci 1994 15(3):71-76.
Gao et al., Reduced fear memory and anxiety-like behavior in mice lacking formylpeptide receptor 1, Behav Genet 2011 41:724-733.
Hayhoe et al., Annexin 1 and its bioactive peptide inhibit neutrophil-endothelium interactions under flow: indication of distinct receptor involvement, Blood 2006 107(5):2123-2130.
Huggins et al., Annexin-1-deficient dendritic cells acquire a mature phenotype during differentiation, FASEB J 2009 23(4):985-996.
Huitinga et al., Effect of annexin-1 on experimental autoimmune encephalomyelitis (EAE) in the rat, Clin Exp Immunol 1998 111(1):198-204.
Iaccarino et al., Anti-annexins autoantibodies: their role as biomarkers of autoimmune disease, Autoimmunity Reviews 10 2011 553:558.
Jacobs et al., Role of IL-2 and IL-4 in exacerbations of murine antigen-induced arthritis, Immunology 1994 83(3):390-396.
John et al., Annexin A1 and the formyl peptide receptor family: neuroendocrine and metabolic aspects, Curr Op Pharm, 2008 8(6):765-776.
Kellner, Drug treatment of obsessive-compulsive disorder, Dialogues Clin Neurosci 2010 187-197.
Lim et al., Promoting detachment of neutrophils adherent to murine postcapillary venules to control inflammation: effect of lipocortin 1, PNAS 1998 95:14535-14539.
Liu et al., Identification of annexin A1 as a proinvasive and prognostic factor for lung adenocarcinoma, Clin Exp Metastasis 2001 28(5):413-425.
Maderna et al., Modulation of phagocytosis of apoptotic neutrophils by supernatant from dexamethasone-treated macrophages and annexin-derived peptide Ac(2-26), J Immunol 2005 174(6):3727-3733.
Maynard et al., Protection against anthrax toxin by recombinant antibody fragments correlates with antigen affinity, Nature Biotech 2002 20(6):597-601.
Non-final Office Action dated Jun. 20, 2014 issued in related U.S. Appl. No. 13/131,927.
Notice of Allowance dated Nov. 9, 2014 cited in related U.S. Appl. No. 13/131,927.
O'Kennedy et al., Antibody engineering: an overview, Abstract, Essays Biochem 1991 26:59-75.
Oliani et al., Annexin 1 localization in tissue eosinophils as detected by electron microscopy, Mediator Inflamm 2002 11(5):287-292.
Owens et al., The genetic engineering of monoclonal antibodies, J Immunol Methods 1994 168(2):149-165.
Paschalidis et al., Modulation of experimental autoimmune encephalomyelitis by endogenous Annexin A1, J Neuroinflammation 2009 6:33.
Paschalidis et al., Role of endogenous Annexin-A1 in the regulation of thymocyte positive and negative selection, Cell Cycle 2010 9(4):785-794.
Paul, Fundamental Immunology, 3rd Edition, 1993, pp. 292-295.
Pepinsky et al., Monoclonal antibodies to lipcortin-1 as probes for biological function, FEBS Lett 1990 261(2):247-252.
Perretti et al., Acute inflammatory response in the mouse: exacerbation by immunoneutralization of lipocortin 1, British J Pharm 1996 117:1145-1154.
Perretti et al., Annexin A1 and glucocorticoids as effectors of the resolution of inflammation, Nature Rev 2009 9(1):62-70.
Rudikoff et al., Single amino acid substitution altering antigen-binding specificity, PNAS 1982 79(6):1979-1983.
Scannell et al., Annexin-1 and peptide derivatives are released by apoptotic cells and stimulate phagocytosis of apoptotic neutrophils by macrophages, J Immunol 2007 178(7):4595-4605.
Solito et al., Annexin A1 in the brain—undiscovered roles?, Trends Pharm Sci 2008 29(3):135-142.
Swanborg et al., Short analytical review, animal models of human disease, experimental autoimmune encephalomyelitis in rodents as a model for human demyelinating disease, Clin Immuno Pathology 1995 77:4-13.
Tagoe et al., Annexin-1 mediates TNF-alpha-stimulated matrix metalloproteinase secretion from rheumatoid arthritis synovial fibroblasts, J Immunol 2008 181(4):2813-2820.
Vajdos et al. Comprehensive functional maps of the antigen-binding site of an anti-ErbB2 antibody obtained with shotgun scanning mutagenesis. J. Mol. Bioi. Jul. 5, 2002, 320(2):415-28.
van Eden et al., Immune regulation in adjuvant-induced arthritis, possible implications for innovative therapeutic strategies in arthritis, Arthriris & Rheumatism 2003 48(7):1788-1796.
Vong et al., Annexin 1 cleavage in activated neutrophils: a pivotal role for proteinase 3, J Biol Cehm 2007 282(41):29998-30004.
Wang et al., Assessing the validity of current mouse genetic models of obsessive-compulsive disorder, Behac Pharm 2009 20:119-133.
Winkler et al., Changing the antigen binding specificity by single point mutations of an anti-p24 (HIV-1) antibody, J Immuno 2000 165(8):4505-4514.
Yang et al., Anti-inflammatory effect of lipcortin 1 in experimental arthritis, Inflammation 1997 21(6):583-596.
Yang et al., Inhibitory effect of annexin 1 on synovial inflammation in rat adjuvant arthritis, Arthritis Rheum 1999 42(7):1538-1544.
Yang et al., Modulation of inflammation and response to dexamethasone by Annexin 1 in antigen-induced arthritis, Arthritis Rheum 2004 50(3):976-984.
Non-Final Office Action dated Nov. 12, 2014 in related U.S. Appl. No. 13/702,593.
Final Office Action dated Feb. 24, 2015 in related U.S. Appl. No. 13/702,593.
Notice of Allowance dated May 1, 2015 in related U.S. Appl. No. 13/702,593.
Pakula et al., Genetic analysis of protein stability and function, Annu Rev Genet 1989 23:289-310.
Schildbach et al., Modulation of antibody affinity by a non-contact residue, Protein Sci 1992 2:206-214.
Hong Xin et al., Hybridoma passage in vitro may result in reduced ability of antimannan abtibody to protect against disseminated candidiasis, Infect Immun 2006 74(7):4310-4321.
Kamaly et al., Development and in vivo efficacy of targeted polymeric inflammation-resolving nanoparticles, PNAS 2013 110(16):6506-6511.
Yao et al., Proteomic analysis for anti-atherosclerotic effect of tetrahydroxystilbene glucoside in rats, Biomedicine & Pharmacotherapy 2013 67(2):140-145.
Purified Mouse Anti-Annexin 1 technical data sheet, BD Transduction Laboratories, 2008.
Benros et al., The epidemiologic evidence linking autoimmune diseases and psychosis, Biol Psychiatry 2014 75:300-306.
Bergink et al., Autoimmunity, inflammation, and psychosis: A search for peripheral markers, Biol Psychiatry 2014 75(4):324-331.
Brod et al., 'As above, so below' examining the interplay between emotion and the immune system, Immunology 2014 143(3):311-318.
Brynskikh et al., Adaptive immunity affects learning behavior in mice, J Brain Behav Immun 2008 22(6):861-869.
Clark et al., A proteome analysis of the anterior cingulate cortex gray matter in schizophrenia, Molecular Psychiatry 2006 11:459-470.
Correia et al., A proteome analysis of the anterior cingulate cortex gray matter in schizophrenia, Molecular Psychiatry 2006 11:459-470.

(56) References Cited

OTHER PUBLICATIONS

D'Acquisto et al., Smile—It's in your blood!, Biochem Pharmacol 2014 91(3):287-292.

D'Acquisto, Editorial overview: Immunomodulation: Exploiting the circle between emotions and immunity: impact on pharmacological treatments, Curr Opin Pharmacol 2016 29:8-12.

Ellwardt et al., Understanding the role of T cells in CNS homeostasis, Trends Immunol 2016 37(2):154-165.

Sperner-Unterweger and Fuchs, Schizophrenia and psychoneuroimmunology: An integrative view, Curr Opin Psychiatry 2015 28(3):201-206.

Sun et al., Annexin-1 is abnormally expressed in Fragile X Syndrome: two-dimensional electrophoresis study in lymphocytes, Am J Med Gene 2001 103:81-90.

Walsh et al., T cells in the central nervous system: messengers of destruction or purveyors of protection?, J Immunology 2014 141(3):340-344.

Official Action dated Jun. 13, 2017 received in related U.S. Appl. No. 14/616,320.

Oliani et al., "Neutrophil Interaction With Inflamed Postcapillary Venule Endothelium Alters Annexin 1 Expression", Am J Pathol, 2001, 158:603-614.

Lupus Erythematosus—Wikipedia https://en.wikipedia.org/wiki/Lupus_erythematosus, Jun. 7, 2017, pp. 1-4.

Office Action dated Jan. 17, 2018 in related U.S. Appl. No. 14/616,320.

Mihaylova et al., "Annexin A1 as a target for managing murine pristane-induced systemic lupus erythematosus", Autoimmunity, 2017, 50(4), pp. 257-268.

Bates et al., "Genetic immunization for antibody generation in research animals by intravenous delivery of plasmid JNA", BioTechniques, 2006, 40(2), pp. 199-207.

Bist et al., "Annexin-A1 regulates TLR-mediated IFN-beta production through an interaction with Tank-binding kinase 1", J Immunol, 2013, 191(8), pp 4375-4382.

Bradyanova et al., Functional elimination of autoreactive T cells by antibody therapy in MRL/LPR murine model of systemic lupus erythematosus, Abstract AO4 in Proceedings of Vth Workshop on Experimental models and methods in biomedical research, Apr. 7-9, 2014, pp 20.

Chipinski et al., Functional elimination of autoreactive T cells by antibody therapy in humanized SCID model of systemic lupus erythematosus, Abstract AO4 in Proceedings of Vth Workshop on Experimental models and methods in biomedical research, Apr. 7-9, 2014, pp 19.

Correia et al., "Recurrent duplications of the annexin A1 gene (ANXA1) in autism spectrum disorders", Molecular Autism, 2014, 5(28), pp. 1-14.

D'Acquisto et al., "Annexin A1: A novel target of the immunosuppressive effects of glucocorticoids in autoimmune diseases", FASEN Journal, 2006, 20(5 (part 2)), pp. A1376.

Ferlazzo et al., Anti-inflammatory effects of annexin-1: stimulation of IL-10 release and inhibition of nitric oxide synthesis, International Immunopharmacology, 2003, 3, pp. 1363-1369.

Xu, G., et al. "Development of High-specificity Antibodies against Renal Urate Transporters Using Genetic mmunization", Journal of Biochemistry and Molecular Biology, 2006, 39(6), pp. 696-702.

Xu. G., et al. "Use of genetic immunization to generate a high-level antibody against rat dicarboxylate transporter", Int Urol Nephrol, 2009, 41, pp. 171-178.

Lerner, "Tapping the immunological repertoire to produce antibodies of predetermined specificity", Nature, 1982, 299, pp. 592-596.

Office Action dated Nov. 9, 2018 in related U.S. Appl. No. 14/616,320.

Final Office Action dated Apr. 2, 2019 from related U.S. Appl. No. 14/616,320, filed Feb. 6, 2015.

Office Action dated Jun. 12, 2019 in related U.S. Appl. No. 15/697,668.

Lee, "Effect of disruption of 3D8 complementarity-determining regions on properties of 3D8 antibody", Dissertation submitted to The Graduate School of Ajou University, 2012, pp. 1-71.

NIH Guidelines for Ascites Production in Mice (available online at https://oacu.oir.nih.gov/sites/default/files/uploads/arac-guidelines/ascites.pdf—accessed Mar. 18, 2019).

Milstein's legacy (available online at http://www.whatisbiotechnology.org/index.php/exhibitions/milsteinilegacy/The-legacy-of-Milsteins-work—accessed Mar. 18, 2019).

L. R. Jackson et al., "Monoclonal Antibody Production in Murine Ascites, II. Production Characteristics" Laboratory Animal Science, 1999, 49(1):81-86.

L. R. Jackson et al. " Monoclonal Antibody Production in Murine Ascites, L Clinical and Pathologic Features", Laboratory Animal Science, 1999, 49(1):70-80.

F. M. Hendriksen et al. "Production of monoclonal antibodies by the ascites method in laboratory animals", Research in Immunology, 1998, 149(6):535-542.

W. M. Yokoyama, "Monoclonal Antibody Supernatant and Ascites Fluid Production", 2000, Current Protocols in Immunology, 2.6.1-2.6.9.

B.R. Brodeur and P.S. Tsang, "High yield monoclonal antibody production in ascites", 1986, Journal of Immunological Methods, 86:239-41.

J. Rescher and V. Gerke, "Annexins—unique membrane binding proteins with diverse functions", 2004, Journal of Cell Science, 117:2631-2639.

A. Hofmann et al., "Interactions of Benzodiazepine Derivatives with Annexins", 1998, The Journal of Biological Chemistry, 273(5):2885-2894.

G. Boulougouris et al., IL-2-Independent Activation and Proliferation in Human T Cells Induced by CD28, 1999, J Immunol., 163(4):1809-1816.

C.H. June et al., "Two Distinct Mechanisms of Interleukin-2 Gene Expression in Human T Lymphocytes", 1989, Journal of Autoimmunity, 2 (Supplement), 55-65.

J.D. Dasgupta et al., "The role of class I histocompatibility antigens in the regulation of T-cell activation", 1987, PNAS, 84:1094-1098.

Notice of Allowance dated Dec. 19, 2019 in related U.S. Appl. No. 15/697,668.

Cited Document A: "Interleukin 2 (IL-2)", 1990, 79, pp. 1343-1347.

Cited Document B: Matsuzaki et al., "Diseases Caused by Disturbance of Th1/Th2 Balance", 2003, 51(1), pp. 9-13.

Hay et al., "The BILAG index: a reliable and valid instrument for measuring clinical disease activity in systemic lupus arythematosus", QJM: An International Journal of Medicine, 1993, 86(7), pp. 447-458.

Isenberg et al., "Fifty years of anti-ds DNA antibodies: Are we approaching journey's end?", Rheumatology, 2007, 46(7), pp. 1052-1056.

Iwata et al., "B-cell subsets, signaling and their roles in secretion of autoantibodies" 2016, Lupus, 28(8), pp. 850-856.

Kaplan et al., "Neutrophil Extracellular Traps: Double-Edged Swords of Innate Immunity", The Journal of mmunology, 2012, 189(6), pp. 2689-2695.

Liu et al., "Specific post-translational histone modifications of neutrophil extracellular traps as immunogens and potential targets of lupus autoantibodies", Arthritis Research and Therapy, 2012, 14(R25).

Matsumoto et al., "Interleukin-10-producing plasmablasts exert regulatory function in autoimmune inflammation", Immunity, 2014, 41(6), pp. 1040-1051.

Pepinsky et al., "Monoclonal antibodies to lipocortin-1 as probes for biological function", FEBS Letters 1990, 261(2), pp. 247-252.

Swaak et al., "Predictive value of complement profiles and anti-dsDNA in systemic lupus erythematosus", Annals of the Rheumatic Diseases, 1986, 45, pp. 359-366.

Thieblemont et al., "Human neutrophils in auto-immunity", Seminars in Immunology, 2016, 28(2), pp. 159-173.

Tsokos, "Systemic lupus erythematosus Mechanism of Disease", The New England Journal of Medicine, 2011, 365, pp. 2110.

* cited by examiner

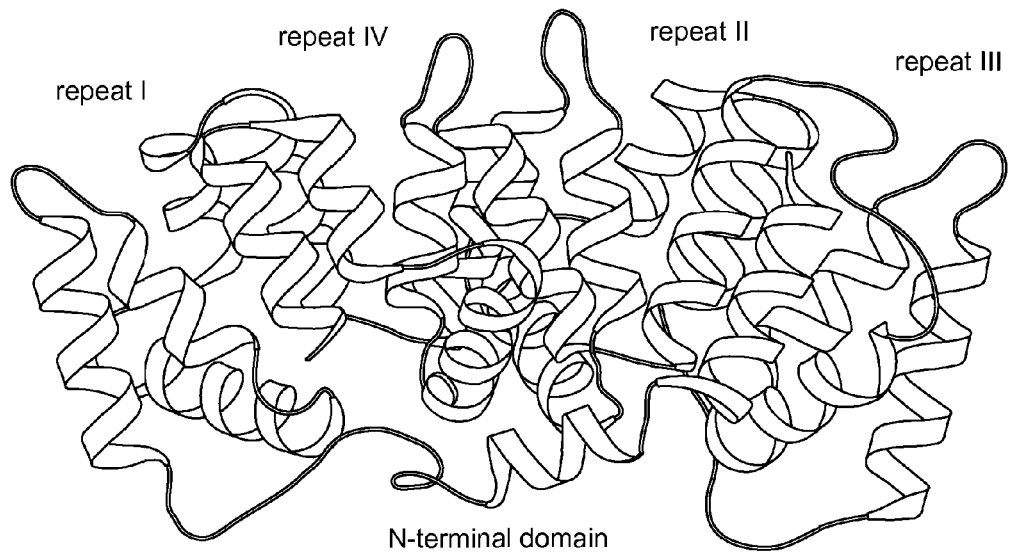
FIG. 1A
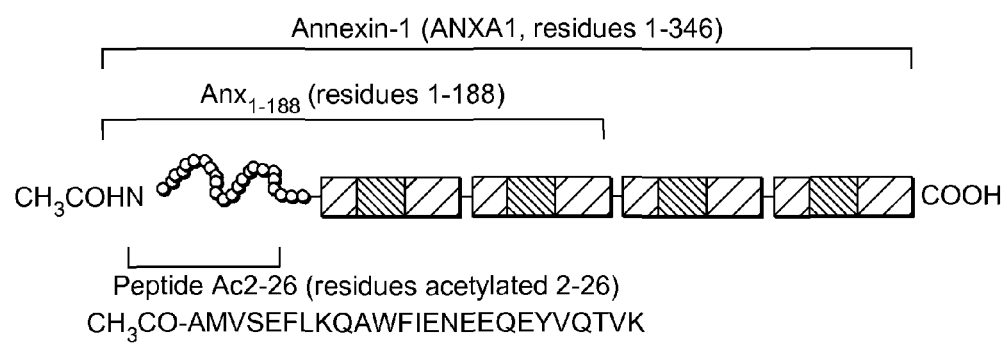
FIG. 1B
CH₃CO-AMVSEFLKQAWFIENEEQEYVQTVK
FIG. 1C (i)

```
1    MAMVSEFLKQ AWFIENEEQE YVQTVKSSKG GPGSAVSPYP
41   TFNPSSDVAA LHKAIMVKGV DEATIIDILT KRNNAQRQQI
81   KAAYLQETGK PLDETLKKAL TGHLEEVVLA LLKTPAQFDA
121  DELRAAMKGL GTDEDTLIEI LASRTNKEIR DINRVYREEL
161  KRDLAKDITS DTSGDFRNAL LSLAKGDRSE DFGVNEDLAD
201  SDARALYEAG ERRKGTDVNV FNTILTTRSY PQLRRVFQKY
241  TKYSKHDMNK VLDLELKGDI EKCLTAIVKC ATSKPAFFAE
281  KLHQAMKGVG TRHKALIRIM VSRSEIDMND IKAFYQKMYG
321  ISLCQAILDE TKGDYEKILV ALCGGN
```

(ii)

```
1    ATGGCAATGG TATCAGAATT CCTCAAGCAG GCCTGGTTTA
41   TTGAAAATGA AGAGCAGGAA TATGTTCAAA CTGTGAAGTC
81   ATCCAAAGGT GGTCCCGGAT CAGCGGTGAG CCCCTATCCT
121  ACCTTCAATC CATCCTCGGA TGTCGCTGCC TTGCATAAGG
161  CCATAATGGT TAAAGGTGTG GATGAAGCAA CCATCATTGA
201  CATTCTAACT AAGCGAAACA ATGCACAGCG TCAACAGATC
241  AAAGCAGCAT ATCTCCAGGA AACAGGAAAG CCCCTGGATG
281  AAACACTGAA GAAAGCCCTT ACAGGTCACC TTGAGGAGGT
321  TGTTTTGGCT CTGCTAAAAA CTCCAGCGCA ATTTGATGCT
361  GATGAACTTC GTGCTGCCAT GAAGGGCCTT GGAACTGATG
401  AAGATACTCT AATTGAGATT TTGGCATCAA GAACTAACAA
441  AGAAATCAGA GACATTAACA GGGTCTACAG AGAGGAACTG
481  AAGAGAGATC TGGCCAAAGA CATAACCTCA GACACATCTG
521  GAGATTTTCG GAACGCTTTG CTTTCTCTTG CTAAGGGTGA
561  CCGATCTGAG GACTTTGGTG TGAATGAAGA CTTGGCTGAT
601  TCAGATGCCA GGGCCTTGTA TGAAGCAGGA GAAAGGAGAA
641  AGGGGACAGA CGTAAACGTG TTCAATACCA TCCTTACCAC
681  CAGAAGCTAT CCACAACTTC GCAGAGTGTT TCAGAAATAC
721  ACCAAGTACA GTAAGCATGA CATGAACAAA GTTCTGGACC
761  TGGAGTTGAA AGGTGACATT GAGAAATGCC TCACAGCTAT
801  CGTGAAGTGC GCCACAAGCA AACCAGCTTT CTTTGCAGAG
841  AAGCTTCATC AAGCCATGAA AGGTGTTGGA ACTCGCCATA
881  AGGCATTGAT CAGGATTATG GTTTCCCGTT CTGAAATTGA
921  CATGAATGAT ATCAAAGCAT TCTATCAGAA GATGTATGGT
961  ATCTCCCTTT GCCAAGCCAT CCTGGATGAA ACCAAAGGAG
1001 ATTATGAGAA AATCCTGGTG GCTCTTTGTG GAGGAAACTA
1041 A
```

*FIG. 2A*

```
1    MAMVSEFLKQ  AWFIENEEQE  YVQTVKSSKG  GPGSAVSPYP
41   TFNPSSDVAA  LHKAIMVKGV  DEATIIDILT  KRNNAQRQQI
81   KAAYLQETGK  PLDETLKKAL  TGHLEEVVLA  LLKTPAQFDA
121  DELRAAMKGL  GTDEDTLIEI  LASRTNKEIR  DINRVYREEL
161  KRDLAKDITS  DTSGDFRNAL  LSLAKGDRSE  DFGVNEDLAD
201  SDARALYEAG  ERRKGTDVNV  FNTILTTRSY  PQLRRVFQKY
241  TKYSKHDMNK  VLDLELKGDI  EKCLTAIVKC  ATSKPAFFAE
281  KLHQAMKGVG  TRHKALIRIM  VSRSEIDMND  IKAFYQKMYG
321  ISLCQAILDE  TKGDYEKILV  ALCGGN
```

FIG. 2B

```
1    MNLILRYTFS  KMAMVSEFLK  QAWFIENEEQ  EYVQTVKSSK
41   GGPGSAVSPY  PTFNPSSDVA  ALHKAIMVKG  VDEATIIDIL
81   TKRNNAQRQQ  IKAAYLQETG  KPLDETLKKA  LTGHLEEVVL
121  ALLKTPAQFD  ADELRAAMKG  LGTDEDTLIE  ILASRTNKEI
161  RDINRVYREE  LKRDLAKDIT  SDTSGDFRNA  LLSLAKGDRS
201  EDFG
```

FIG. 2C

```
1    MAMVSEFLKQ  AWFIENEEQE  YVQTVKSSKG  GPGSAVSPYP
41   TFNPSSDVAA  LHKAIMVKGV  DEATIIDILT  KRNNAQRQQI
81   KAAYLQETGK  PLDETLKKAL  TGHLEEVVLA  LLKTP
```

FIG. 2D

| | | Antibody production by genetic immunisation - the direct way from gene to antibody |
|---|---|---|
| ✓ | —▭— | |
| ✓ | ◯ | ▶ Cloning of the cDNA into a GENOVAC expression vector and confirmation of cell-surface expression |
| | 🔍○○○ | ▶ Several intradermal applications of vector DNA absorbed to gold particles |
| | 🐭 | ▶ Mouse cells take up the immunisation vector and express the cDNA-encoded foreign protein, stimulating an immune response |
| | | ▶ Fusion of mouse lymphocytes with murine myeloma cells to produce hybridomas |
| | | ▶ Specificity testing, cloning of hybridomas, and production of monoclonal antibodies |
| | | |

*FIG. 3A*

```
1              10              20 23        30       35      40
NIVMTQSPKSMSMSVGERVTLTC|KASENVVTYVS|WYQQKP
    Framework 1                    CDR1

41            50       57 60             70              80
EQSPKLLIY|GASNRYT|GVPDRFTGSGSATDFTLTISSVQA
  Framework 2  CDR2          Framework 3

81          88            98         107        115
EDLADYHC|GQGYSYPYT|FGGGTKLEIK|RADAAPTV|
              CDR3         J region    C Kappa
```

FIG. 5

```
1          10           20    25    30      36   40
QVQLQQSGPELVRPGTSVKMSCKAS GYTFTNYWIG WAKQR
        Framework 1                CDR1

41         50 52a        60    66   70           80
PGHGLEWIG DIYPGGDYTNYNEKFKG KATLTADKSSSTAYM
Framework 2       CDR2              Framework 3

81 82abc       90   94    100a  103        113
QFSSLTSEDSAIYYCAR WGLGYYFDY WGQGITLTVSS AKTTP
                     CDR3       J region       CH1
```

METHODS OF TREATING OBSESSIVE COMPULSIVE DISORDER (OCD) OR ANXIETY USING AN ANTIBODY THAT BINDS TO ANNEXIN-1

FIELD OF THE INVENTION

The present invention relates to the use of specific binding molecules, particularly antibodies and fragments thereof, which bind to annexin-A1, in the treatment of obsessive-compulsive disorder (OCD) and related diseases.

BACKGROUND TO THE INVENTION

Obsessive compulsive disorder (OCD) is a chronic, relapsing psychiatric affliction with a lifetime prevalence of 1-3%. According to the Diagnostic and Statistical Manual of Mental Disorders (4th ed; DSM IV), the essential features of this disease are recurrent obsessions and/or compulsions (e.g., doubting, checking, washing) that are time consuming (i.e., they take more than 1 hour a day) or cause marked distress or significant impairment.

The most effective treatments for mental disorders like OCD are antipsychotic and behavioural treatments. Yet, around 30% of the patients are refractory to pharmaco- and behavioural therapy. In addition, side effects such as agranulocytosis (loss of the white blood cells that help a person fight infection) and changes in a person's metabolism (leading to diabetes) are serious problems that limit the use of these drugs. There is therefore a need in the art for a therapy for such diseases that does not have these unwanted side effects.

SUMMARY OF THE INVENTION

The present inventors have previously discovered that antibodies that bind to a protein called Annexin-1 (Anx-A1) are useful in the treatment of T cell-mediated diseases. This is the subject of the PCT application published as WO 2010/064012. The inventors have also produced a monoclonal antibody that binds to Anx-A1 and has excellent properties in terms of specific inhibition of T cell activation without any adverse cytotoxic effects. This antibody is the subject of the PCT application published as WO 2011/154705. The inventors have now surprisingly found that antibodies that bind to Anx-A1 are useful in the treatment of OCD and related diseases.

Accordingly, in a first aspect the present invention provides a specific binding molecule that binds to Annexin-1 (Anx-A1) for use in the treatment of obsessive compulsive disorder (OCD) or a disease related to OCD. In one embodiment, the present invention provides a specific binding molecule raised against the human Anx-A1 protein having the amino acid sequence shown in FIG. 2A for use in the treatment of obsessive compulsive disorder (OCD) or a disease related to OCD.

DEFINITIONS

As used herein, a "specific binding molecule" is a member of a pair of molecules which have binding specificity for one another. The members of a specific binding pair may be naturally derived or wholly or partially synthetically produced. One member of the pair of molecules has an area on its surface, which may be a protrusion or a cavity, which specifically binds to and is therefore complementary to a particular spatial and polar organisation of the other member of the pair of molecules. Thus, the members of the pair have the property of binding specifically to each other. Examples of types of specific binding pairs are antigen-antibody, biotin-avidin, hormone-hormone receptor, receptor-ligand and enzyme-substrate. The present invention is generally concerned with antigen-antibody type reactions. The specific binding molecule used in the present invention binds with greater affinity to Anx-A1 than to other molecules, i.e. it binds specifically to Anx-A1. Specific binding molecules which bind to Anx-A1 include anti-Anx-A1 antibodies and aptamers. The specific binding molecule used in the present invention is typically an antibody.

The term "antibody" as used herein refers to immunoglobulin molecules and immunologically active portions of immunoglobulin molecules, i.e., molecules that contain an antigen binding site that specifically binds an antigen, whether natural or partly or wholly synthetically produced. The term also covers any polypeptide or protein having a binding domain which is, or is homologous to, an antibody binding domain. These can be derived from natural sources, or they may be partly or wholly synthetically produced. Antibodies are polypeptides that typically contain two identical heavy chains and two identical light chains, which are smaller than the heavy chains. In mammals there are two types of light chain, which are called lambda ($\lambda$) and kappa ($\kappa$). Each of the heavy chains and each of the light chains are composed of a variable region and a constant region. The heavy chain variable region is referred to as the $V_H$ region and the light chain variable region is referred to as the $V_L$ region. For kappa light chains, the $V_L$ region can also be referred to as the $V_K$ region. Each of the variable regions of the heavy and light chains comprise three complementarity determining regions (CDRs), CDR1, CDR2 and CDR3. These are named VLCDR1, VLCDR2, VLCDR3, VHCDR1, VHCDR2 and VHCDR3 respectively. Examples of antibodies are the immunoglobulin isotypes (e.g., IgG, IgE, IgM, IgD and IgA) and their isotypic subclasses; fragments which comprise an antigen binding domain such as Fab, F(ab')$_2$, Fv, scFv, dAb, Fd; and diabodies. Antibodies may be polyclonal or monoclonal. A monoclonal antibody may be referred to herein as "mAb".

DETAILED DESCRIPTION OF THE INVENTION

Annexins are a group of calcium- and phospholipid-binding cellular proteins and are also known as lipocortins. The annexin family has 13 members in humans, including Annexin A1, Annexin A2 and Annexin A5. Annexin-A1 is also known as Annexin-1 and is referred to herein as "Anx-A1". Human annexin-1 (Anx-A1) is a 37-kDa protein and was originally described as a mediator of the actions of glucocorticoids. Over the last few years evidence has shown than Anx-A1 plays a homeostatic role in the adaptive immune system, in particular T cells, by modulating the strength of T cell receptor (TCR) signalling. Anx-A1 acts as an endogenous down-regulator of inflammation in cells of the innate immune system in vivo. FIG. 1A is a ribbon diagram showing the three-dimensional structure of Anx-A1.

There are eight human nucleotide sequences which encode Anx-A1. Of these, only four are translated and thus there are four isoforms of Anx-A1, designated ANXA1-002, ANXA1-003, ANXA1-004 and ANXA1-006. These sequences are available from the Ensembl website (www-.ensembl.org) and are designated ENSP00000257497 (ANXA1-002), ENSP00000366109 (ANXA1-003), ENSP00000412489 (ANXA1-004) and ENSP00000414013 (ANXA1-006). The amino acid and nucleotide sequences of one isoform of human Annexin-1 (Anx-A1), ANXA1-003, are shown in FIG. 2A. The amino acid sequences of isoforms ANXA1-002, ANXA1-004 and ANXA1-006 are shown in FIGS. 2B, 2C and 2D respectively. As can be seen from FIG. 2, isoforms ANXA1-002, ANXA1-004 and ANXA1-006 are either short splice variants of ANXA1-003 or variants of ANXA1-003 with a small number of amino acid changes.

A number of studies have shown that an N-terminal peptide of Anx-A1 named Ac.2-26 acts as a bioactive surrogate of the whole protein (see e.g. Lim et al., Proc Natl Acad Sci USA 95, 14535-9, 1998).

FIG. 1B is a schematic representation of the annexin repeats and the location of this bioactive sequence. Peptide Ac.2-26 is an acetylated peptide having the sequence of amino acid residues 2-26 of the full-length amino acid sequence of Anx-A1 shown in FIG. 2. The sequence of peptide Ac.2-26 is shown in FIG. 1C and is as follows:

```
                                          (SEQ ID NO: 1)
CH3CO-AMVSEFLKQAWFIENEEQEYVQTVK
```

Anx-A1 and its N-terminal derived bioactive peptides mediate their biological effects through members of the formyl peptide receptor (FPR) family. The full-length protein Anx-A1 exerts its counterregulatory actions on neutrophil extravasation and innate immunity by direct binding and activation of one member of this family, formyl peptide receptor like-1 (FPRL-1), also known as formyl peptide receptor 2 (FPR-2/ALX). The present inventors have previously found that stimulation of T cells in the presence of hrAnx-A1 increases T cell activation via stimulation of FPRL-1/FPR-2/ALX (D'Acquisto et al., Blood 109: 1095-1102, 2007).

The specific binding molecule used in the present invention binds to Annexin-1 (Anx-A1). The Anx-A1 to which the specific binding molecule binds is typically human Anx-A1 having the polypeptide sequence shown in FIG. 2A, or a variant thereof such as one of the isoforms of human Anx-A1 having the polypeptide sequence shown in FIG. 2B or FIG. 2C, or a fragment thereof such as the polypeptide having the sequence shown in FIG. 1C or the isoform of human Anx-A1 having the polypeptide sequence shown in FIG. 2D. The Anx-A1 to which the specific binding molecule binds is typically encoded by the nucleotide sequence shown in FIG. 2A. The specific binding molecule is typically an antibody.

Anti-Anx-A1 antibodies can be raised, for example, against human Anx-A1 having a polypeptide sequence set out in FIG. 2A, 2B, 2C or 2D, typically the polypeptide sequence set out in FIG. 2A. Alternatively, anti-Anx-A1 antibodies can be directed to a particular epitope or epitopes of human Anx-A1 having an amino acid sequence set out in FIG. 2. For example, anti-Anx-A1 antibodies can be directed against an N-terminal fragment of Anx-A1, for example an N-terminal fragment of at least 188, 100, 50 or 25 amino acid residues from the N-terminus of the amino acid sequence set out in FIG. 2A. Alternatively, the anti-Anx-A1 antibody for use in the invention is an antibody raised against the N-terminal fragment of Anx-A1 termed Act-26 and which has the sequence shown in FIG. 1C or against a fragment of at least 6 amino acids thereof. Specific binding molecules which bind to Anx-A1 therefore include anti-Anx-A1 antibodies which are antibodies against the Anx-A1 fragment Ac2-26 having the sequence shown in FIG. 1C or a fragment of at least 6, at least 7, at least 8, at least 9, at least 10, at least 15, at least 20, at least 21, at least 22, at least 23 or at least 24 amino acids thereof. In this embodiment, the anti-Anx-A1 antibody is raised against a fragment of the sequence shown in FIG. 1C which is antigenic and capable of stimulating the production of antibodies which, when administered, can be used in the treatment of OCD and related diseases.

In a first aspect, the present invention provides a specific binding molecule that binds to Annexin-1 (Anx-A1) for use in the treatment of obsessive compulsive disorder (OCD) or a disease related to OCD. In one embodiment, the present invention provides a specific binding molecule raised against the human Anx-A1 protein having the amino acid sequence shown in FIG. 2A for use in the treatment of obsessive compulsive disorder (OCD) or a disease related to OCD.

This aspect of the invention also extends to the use of a specific binding molecule comprising the Complementarity Determining Regions (CDRs) VLCDR1, VLCDR2, VLCDR3, VHCDR1, VHCDR2 and VHCDR3 of the specific binding molecule as defined in relation to the first aspect of the invention or an amino acid sequence at least 70% identical to each of the respective CDRs. The specific binding molecule is typically an antibody.

In one embodiment, the specific binding molecule comprises Complementarity Determining Regions (CDRs) VLCDR1, VLCDR2, VLCDR3, VHCDR1, VHCDR2 and VHCDR3, each having a respective amino acid sequence as follows in which

```
                                          (SEQ ID NO: 2)
         VLCDR1 is KASENVVTYVS (SEQ ID NO: 3)
         VLCDR2 is GASNRYT (SEQ ID NO: 4)
         VLCDR3 is GQGYSYPYT (SEQ ID NO: 5)
         VHCDR1 is GYTFTNYWIG (SEQ ID NO: 6)
         VHCDR2 is DIYPGGDYTNYNEKFKG (SEQ ID NO: 7)
         VHCDR3 is WGLGYYFDY
``` or an amino acid sequence at least 70% identical thereto.

The CDRs are designated according to a combination of conserved sequence definition (Rabat et al in "Sequences of Proteins of Immunological Interest", Nat'l. Inst. Health, Bethesda, Md. (1987)), and structural definition (Chothia and Lesk *J. Mol Biol.* 196:901-17(1987)). These definitions were also subsequently described in Carter et al, *Proc Nat'l Acad Sci USA.* 89:4285-9 (1992).

The present invention also extends to the use of variants of protein, polypeptide and peptide sequences referred to herein. As used herein the term "variant" relates to proteins, polypeptides and peptides which have a similar amino acid sequence and/or which retain the same function. For instance, the term "variant" encompasses proteins, polypeptides and peptides which include one or more amino acid additions, deletions, substitutions or the like. An example of a variant of the present invention is a protein, such as a fusion protein, comprising a peptide as defined above, apart from the substitution of one or more amino acids with one or more other amino acids. The skilled person is aware that various amino acids have similar properties. One or more such amino acids of a substance can often be substituted by one or more other such amino acids without eliminating a desired activity of that substance.

Thus the amino acids glycine, alanine, valine, leucine and isoleucine can often be substituted for one another (amino acids having aliphatic side chains). Of these possible substitutions it is preferred that glycine and alanine are used to substitute for one another (since they have relatively short side chains) and that valine, leucine and isoleucine are used to substitute for one another (since they have larger aliphatic side chains which are hydrophobic). Other amino acids which can often be substituted for one another include: phenylalanine, tyrosine and tryptophan (amino acids having aromatic side chains); lysine, arginine and histidine (amino acids having basic side chains); aspartate and glutamate (amino acids having acidic side chains); asparagine and glutamine (amino acids having amide side chains); and cysteine and methionine (amino acids having sulphur containing side chains).

Substitutions of this nature are often referred to as "conservative" or "semi-conservative" amino acid substitutions.

The present invention therefore extends to the use of a specific binding molecule that binds to Annexin-1 (Anx-A1) having the polypeptide sequence shown in FIG. 2A, or to a variant thereof having the polypeptide sequence shown in FIG. 2B or FIG. 2C, or to a fragment thereof having the polypeptide sequence shown in FIG. 1C or FIG. 2D but with one or more conservative substitutions in any of the respective sequences.

The present invention also extends to the use of a specific binding molecule comprising CDRs having the amino acid sequences described above but with one or more conservative substitutions in the CDRs, such that the amino acid sequences of the CDRs have at least 70% identity to those described above. For example, each CDR may have 1, 2, 3, 4 or 5 conservative substitutions (depending on the CDR) compared to the amino acid sequences of the CDRs set out above. For example, there can be 1, 2 or 3 conservative substitutions in the amino acid sequence of VLCDR1 set out above, 1 or 2 conservative substitutions in the amino acid sequence of VLCDR2 set out above, 1 or 2 conservative substitutions in the amino acid sequence of VLCDR3 set out above, 1, 2 or 3 conservative substitutions in the amino acid sequence of VHCDR1 set out above, 1, 2, 3, 4 or 5 conservative substitutions in the amino acid sequence of VHCDR2 set out above and 1, 2 or 3 conservative substitutions in the amino acid sequence of VHCDR3 set out above, and the sequence will still retain at least 70% identity to the CDR sequences set out above.

Using the three letter and one letter codes the amino acids may be referred to as follows: glycine (G or Gly), alanine (A or Ala), valine (V or Val), leucine (L or Leu), isoleucine (1 or Ile), proline (P or Pro), phenylalanine (F or Phe), tyrosine (Y or Tyr), tryptophan (W or Trp), lysine (K or Lys), arginine (R or Arg), histidine (H or His), aspartic acid (D or Asp), glutamic acid (E or Glu), asparagine (N or Asn), glutamine (Q or Gln), cysteine (C or Cys), methionine (M or Met), serine (S or Ser) and Threonine (T or Thr). Where a residue may be aspartic acid or asparagine, the symbols Asx or B may be used. Where a residue may be glutamic acid or glutamine, the symbols Glx or Z may be used. References to aspartic acid include aspartate, and glutamic acid include glutamate, unless the context specifies otherwise.

Amino acid deletions or insertions can also be made relative to the amino acid sequence for the protein, such as a fusion protein, referred to above. Thus, for example, amino acids which do not have a substantial effect on the activity of the polypeptide, or at least which do not eliminate such activity, can be deleted. Such deletions can be advantageous since the overall length and the molecular weight of a polypeptide can be reduced whilst still retaining activity. This can enable the amount of polypeptide required for a particular purpose to be reduced—for example, dosage levels can be reduced.

Amino acid insertions relative to the sequence of the fusion protein above can also be made. This can be done to alter the properties of a substance of the present invention (e.g. to assist in identification, purification or expression).

Amino acid changes relative to the sequence given above can be made using any suitable technique e.g. by using site-directed mutagenesis or solid state synthesis.

It should be appreciated that amino acid substitutions or insertions within the scope of the present invention can be made using naturally occurring or non-naturally occurring amino acids. Whether or not natural or synthetic amino acids are used, it is preferred that only L-amino acids are present.

"Identity", as will be known to a person of skill in the art, is the relationship between two or more polynucleotide sequences or two or more polypeptide sequences, as determined by comparing the sequences, typically along their whole length. In the art, identity also means the degree of sequence relatedness between polynucleotide or polypeptide sequences, as the case may be, as determined by the match between strings of such sequences. While there exist a number of methods to measure identity between two polynucleotide or two polypeptide sequences, methods commonly employed to determine identity are codified in computer programs.

Computational approaches to sequence alignment generally fall into two categories: global alignments and local alignments. A global alignment attempts to align every residue in every sequence and thus forces the alignment to span the entire length of all query sequences. Global alignments are most useful when the sequences in the query set are similar and of approximately equal size. A general global alignment technique is the Needleman-Wunsch algorithm, which is based on dynamic programming. In contrast, local alignments identify regions of similarity within long sequences that can be widely divergent overall. Local alignments are often preferable, but can be more difficult to calculate because of the additional challenge of identifying the regions of similarity. Local alignments are more useful for dissimilar sequences that are suspected to contain regions of similarity or similar sequence motifs within a larger sequence. The Smith-Waterman algorithm is a general local alignment method and is also based on dynamic programming. With sufficiently similar sequences, there is no difference between local and global alignments. Hybrid methods, known as semiglobal or "glocal" (short for global-local) methods, attempt to find the best possible alignment that includes the start and end of one or the other sequence. This can be especially useful when the downstream part of one sequence overlaps with the upstream part of the other sequence.

Preferred computer programs to determine identity between two sequences include, but are not limited to, BLAST (Altschul et al., J. Mol. Biol. 215, 403 (1990), available at http://blast.ncbi.nlm.nih.gov/Blast.cgi), including BLASTp (for proteins), BLASTn and BLASTx (for nucleotides), gapped BLAST and PSI-BLAST (for proteins, Altschul et al., Nucleic Acids Research 25 (17): 3389-402, 1997), PASTA (available at http://www.ebi.ac.uk/Tools/ sss/), ClustalW/ClustalX (Thompson et al., Nucleic Acids Research 22 (22): 4673-4680 (1994), latest version is 2.1) and the GCG program package (Devereux et al., Nucleic Acids Research, 12, 387 (1984)).

The Clustal program can be used to compare both nucleotide and amino acid sequences. This program compares sequences and finds the optimal alignment by inserting spaces in either sequence as appropriate. It is possible to calculate amino acid identity or similarity (identity plus conservation of amino acid type) for an optimal alignment. A program like BLASTx will align the longest stretch of similar sequences and assign a value to the fit. It is thus possible to obtain a comparison where several regions of similarity are found, each having a different score. Both types of identity analysis are contemplated in the present invention.

The percent identity of two amino acid sequences or of two nucleic acid sequences can be determined by aligning the sequences for optimal comparison purposes (e.g., gaps can be introduced in the first sequence for best alignment with the sequence) and comparing the amino acid residues or nucleotides at corresponding positions. The "best alignment" is an alignment of two sequences which results in the highest percent identity. The percent identity is determined by the number of identical amino acid residues or nucleotides in the sequences being compared (i.e., % identity=number of identical positions/total number of positions×100).

As described above, the determination of percent identity between two sequences can be accomplished using a mathematical algorithm known to those of skill in the art. An example of a mathematical algorithm for comparing two sequences is the algorithm of Karlin and Altschul (1990) Proc. Natl. Acad. Sci. USA 87:2264-2268, modified as in Karlin and Altschul (1993) Proc. Natl. Acad. Sci. USA 90:5873-5877. The BLASTn and BLASTx programs of Altschul, et al. (1990) J. Mol. Biol. 215:403-410 have incorporated such an algorithm. BLAST nucleotide searches can be performed with the BLASTn program, score=100, wordlength=12 to obtain nucleotide sequences homologous to nucleic acid molecules of the invention. BLAST protein searches can be performed with the BLASTp program, score=50, wordlength=3 to obtain amino acid sequences homologous to protein molecules of the invention. To obtain gapped alignments for comparison purposes, Gapped BLAST can be utilised as described in Altschul et al. (1997) Nucleic Acids Res. 25:3389-3402. Alternatively, PSI-Blast can be used to perform an iterated search which detects distant relationships between molecules (Id.). When utilising BLAST, Gapped BLAST, and PSI-Blast programs, the default parameters of the respective programs (e.g., BLASTx and BLASTn) can be used. See http://www.ncbi.nlm.nih.gov. Another example of a mathematical algorithm utilised for the comparison of sequences is the algorithm of Myers and Miller, CABIOS (1989). The ALIGN program (version 2.0) which is part of the CGC sequence alignment software package has incorporated such an algorithm. Other algorithms for sequence analysis known in the art include ADVANCE and ADAM as described in Torellis and Robotti (1994) Comput. Appl. Biosci., 10:3-5; and FASTA described in Pearson and Lipman (1988) Proc. Natl. Acad. Sci. 85:2444-8. Within FASTA, ktup is a control option that sets the sensitivity and speed of the search.

As defined herein, variants of a particular protein, polypeptide or peptide described herein should retain the function of the original protein, polypeptide or peptide. Alternatively or in addition to retaining the function of the original protein, polypeptide or peptide, variants of the proteins, polypeptides or peptides typically share at least 70% sequence identity with the proteins, polypeptides or peptides described herein.

The present invention therefore extends to the use of a specific binding molecule that binds to a sequence having at least 70% identity, using the default parameters of the BLAST computer program (Altschul et al., 0.1. Mol. Biol. 215, 403-410 (1990)) provided by HGMP (Human Genome Mapping Project), at the amino acid level, to the polypeptide sequence shown in FIG. 2A, or to a variant thereof having the polypeptide sequence shown in FIG. 2B or FIG. 2C, or to a fragment thereof having the polypeptide sequence shown in FIG. 1C or FIG. 2D. More typically, the specific binding molecule binds to a sequence that has at least 75%, 80%, 82%, 83%, 85%, 90%, 91%, 92%, 93%, 94%, 95%, 96%, 97%, 98% or at least 99% identity, at the amino acid level, to any of the sequences shown in FIG. 2A, 2B, 2C, 2D or 1C.

Typically, the amino acid sequence of the CDRs of the specific binding molecule used in the invention have at least 70% identity, using the default parameters of the BLAST computer program (Altschul et al., 3. Mol. Biol. 215, 403-410 (1990)) provided by HOMP (Human Genome Mapping Project), at the amino acid level, to the amino acid sequences of the CDRs described above. More typically, the CDR sequence has at least 75%, 80%, 82%, 83%, 85%, 90%, 91%, 92%, 93%, 94%, 95%, 96%, 97%, 98% or at least 99% identity, at the amino acid level, to the sequences shown above. Typically, each of the CDR sequences of the specific binding molecule used in the invention has this level of identity to the amino acid sequences of the CDRs set out above. Alternatively, any 1, 2, 3 4 or 5 of the CDRs of the specific binding molecule used in the invention has this level of identity to the amino acid sequences of the CDRs set out above.

The specific binding molecule used in the invention is typically an antibody, more typically a monoclonal antibody. In one embodiment, the monoclonal antibody used in the present invention is humanised.

The monoclonal antibody used in the present invention can be humanised by modifying the amino acid sequence of the antibody. Methods to reduce the immunogenicity of the specific binding molecules of the invention include CDR grafting on to a suitable antibody framework scaffold or variable surface residues remodelling, e.g. by site-directed mutagenesis or other commonly used molecular biological techniques (Roguska et at *Protein Eng.* 9 895-904 (1996)).

Other methods applicable can include the identification of potential 1-cell epitopes within the molecule, and the subsequent removal of these e.g. by site-directed mutagenesis (de-immunisation). Humanisation of the specific binding molecule may be desired where the molecule is to be used as a therapeutic agent. Humanisation of the CDR regions or of the surrounding framework sequence can be carried out as desired.

It is possible to take monoclonal and other antibodies and use techniques of recombinant DNA technology to produce other antibodies or chimeric molecules which retain the specificity of the original antibody. Such techniques may involve introducing DNA encoding the immunoglobulin variable region, or the complementary determining regions (CDRs), of an antibody to the constant regions, or constant regions plus framework regions, of a different immunoglobulin. See, for instance, EP-A-184187, GB 2188638A or EP-A-239400. A hybridoma or other cell producing an antibody may be subject to genetic mutation or other changes, which may or may not alter the binding specificity of antibodies produced.

As antibodies can be modified in a number of ways, the term "antibody" should be construed as covering any specific binding member or substance having a binding domain with the required specificity. Thus, this term covers antibody fragments, derivatives, functional equivalents and homologues of antibodies, humanised antibodies, including any polypeptide comprising an immunoglobulin binding domain, whether natural or wholly or partially synthetic. Chimeric molecules comprising an immunoglobulin binding domain, or equivalent, fused to another polypeptide are therefore included. Cloning and expression of chimeric antibodies are described in EP-A-0120694 and EP-A-0125023. A humanised antibody may be a modified antibody having the variable regions of a non-human, e.g. murine, antibody and the constant region of a human antibody. Methods for making humanised antibodies are described in, for example, U.S. Pat. No. 5,225,539

The specific binding molecule used in the invention can be a fragment of an antibody. It has been shown that fragments of a whole antibody can perform the function of binding antigens. Examples of binding fragments are (i) the Fab fragment consisting of $V_L$, $V_H$, $C_L$ and $C_H1$ domains; (ii) the Fd fragment consisting of the $V_H$ and $C_H1$ domains; (iii) the Fv fragment consisting of the $V_L$ and $V_H$ domains of a single antibody; (iv) the dAb fragment (Ward, E. S. et al., Nature 341:544-546 (1989)) which consists of a $V_H$ domain; (v) isolated CDR regions; (vi) F(ab')$_2$ fragments, a bivalent fragment comprising two linked Fab fragments; (vii) single chain Fv molecules (scFv), wherein a $V_H$ domain and a $V_L$ domain are linked by a peptide linker which allows the two domains to associate to form an antigen binding site (Bird et al., Science 242:423-426 (1988); Huston et al., PNAS USA 85:5879-5883 (1988)); (viii) bispecific single chain Fv dimers (PCT/US92/09965) and (ix) "diabodies", multivalent or multispecific fragments constructed by gene fusion (WO94/13804; P. Hollinger et al., Proc. Natl. Acad. Sci. USA 90: 6444-6448 (1993)). Typically, the fragment is a Fab, F(ab')$_2$ or Fv fragment or an scFv molecule.

Diabodies are multimers of polypeptides, each polypeptide comprising a first domain comprising a binding region of an immunoglobulin light chain and a second domain comprising a binding region of an immunoglobulin heavy chain, the two domains being linked (e.g. by a peptide linker) but unable to associated with each other to form an antigen binding site: antigen binding sites are formed by the association of the first domain of one polypeptide within the multimer with the second domain of another polypeptide within the multimer (WO94/13804).

Where bispecific antibodies are to be used, these may be conventional bispecific antibodies, which can be manufactured in a variety of ways (Hollinger & Winter, Current Opinion Biotechnol. 4:446-449 (1993)), e.g. prepared chemically or from hybrid hybridomas, or may be any of the bispecific antibody fragments mentioned above. It may be preferable to use scFv dimers or diabodies rather than whole antibodies. Diabodies and scFv can be constructed without an Fc region, using only variable domains, potentially reducing the effects of anti-idiotypic reaction. Other forms of bispecific antibodies include the single chain "Janusins" described in Traunecker et al., EMBO Journal 10:3655-3659 (1991).

Bispecific diabodies, as opposed to bispecific whole antibodies, may also be useful because they can be readily constructed and expressed in E. coli. Diabodies (and many other polypeptides such as antibody fragments) of appropriate binding specificities can be readily selected using phage display (WO94/13804) from libraries. If one arm of the diabody is to be kept constant, for instance, with a specificity directed against antigen X, then a library can be made where the other arm is varied and an antibody of appropriate specificity selected.

The Complementarity Determining Regions (CDRs) VLCDR1, VLCDR2, VLCDR3, VHCDR1, VHCDR2 and VHCDR3 set out above are those of the monoclonal antibody VJ-4B6 produced by the present inventors. Monoclonal antibody VJ-4B6 is described and claimed in International patent application no. PCT/GB2011/000876, published as WO 2011/154705 and which is incorporated herein in its entirety by reference.

The monoclonal antibody VJ-4B6 was produced by a method described in FIG. 3A and in Example 1 herein. Briefly, cDNA encoding full-length human Anx-A1 having the sequence shown in FIG. 2A was cloned into an expression vector and cell-surface expression confirmed. Several intradermal applications of vector DNA adsorbed to gold particles were then administered to mice. The mouse cells took up the immunization vector and expressed the cDNA-encoded protein, stimulating an immune response. Mouse lymphocytes were then fused with murine myeloma cells to produce hybridomas. Specificity testing was then carried out, the hybridomas cloned and the monoclonal antibody produced.

Monoclonal antibody VJ-4B6 is secreted by the hybridoma cell line VJ-4B6-E5-B10-D4 deposited on 3 Jun. 2010 with the European Collection of Cell Cultures (ECACC), Health Protection Agency, Centre for Emergency Preparedness and Response, Porton Down, Salisbury, SP4 0JG, United Kingdom, under the Budapest Treaty, and designated by the accession no. 10060301.

The deposit was made by Fulvio D'Acquisto, Queen Mary and Westfield College, Centre for Biochemical Pharmacology, Charterhouse Square, London EC1M 6BQ. The depositor has authorised the applicant to refer to the deposited material in the application and has given his unreserved and irrevocable consent to the deposited material being made available to the public in accordance with Rule 31(1)(d) of the European Patent Convention.

The hybridoma cell line VJ-4B6-E5-B10-D4 produces the monoclonal antibody VJ-4B6 that specifically binds to Annexin-A1. The monoclonal antibody VJ-4B6 is of the IgG2b isotype.

The antibody VJ-4B6 was raised against the full-length human Anx-A1 protein having the amino acid sequence shown in FIG. 2A.

The DNA and amino acid sequence of the light chain variable region of the antibody VJ-4B6 are shown in FIG. 4. FIG. 5 shows the amino acid sequence of the light chain variable region of VJ-4B6 with the CDRs annotated. FIG. 5 also shows the first few amino acids of the light chain constant region of VJ-4B6.

The DNA and amino acid sequence of the heavy chain variable region of the antibody VJ-4B6 are shown in FIG. 6. FIG. 7 shows the amino acid sequence of the heavy chain variable region of VJ-4B6 with the CDRs annotated. FIG. 7 also shows the first few amino acids of the heavy chain constant region of VJ-4B6.

The CDRs of the antibody VJ-4B6 are as follows:

```
                           (SEQ ID NO: 2)
VLCDR1 is KASENVVTYVS (SEQ ID NO: 3)
VLCDR2 is GASNRYT (SEQ ID NO: 4)
VLCDR3 is GQGYSYPYT (SEQ ID NO: 5)
VHCDR1 is GYTFTNYWIG (SEQ ID NO: 6)
VHCDR2 is DIYPGGDYTNYNEKFKG (SEQ ID NO: 7)
VHCDR3 is WGLGYYFDY
```

The present invention extends to the use of specific binding molecules having the CDRs of the antibody VJ-4B6, as described herein, and also to the use of specific binding molecules having CDRs with at least 70% identity, preferably at least 75%, 80%, 82%, 83%, 85%, 90%, 91%, 92%, 93%, 94%, 95%, 96%, 97%, 98% or at least 99% identity, to one or more of the CDRs of the antibody VJ-4B6, as described herein.

The present invention also extends to the use of specific binding molecules having either the light chain variable region, the heavy chain variable region or both the light chain variable region and the heavy chain variable region of the antibody VJ-4B6 and to variants and fragments of the light chain variable region and/or the heavy chain variable region thereof, as described herein.

In a specific embodiment, the present invention therefore provides a specific binding molecule for use in accordance with the first aspect of the invention comprising a polypeptide having an amino acid sequence as shown in FIG. 4 and/or FIG. 6 or an amino acid sequence having at least 75%, 80%, 82%, 83%, 85%, 90%, 91%, 92%, 93%, 94%, 95%, 96%, 97%, 98% or at least 99% identity to either thereof.

This embodiment of the invention also extends to the use of certain antibody fragments which contain the light chain variable region having the amino acid sequence shown in FIG. 4 and/or the heavy chain variable region having the amino acid sequence shown in FIG. 6 or an amino acid sequence having at least 75%, 80%, 82%, 83%, 85%, 90%, 91%, 92%, 93%, 94%, 95%, 96%, 97%, 98% or at least 99% identity to any such fragments. For example, this embodiment extends to the use of Fab, F(ab')$_2$ or Fv fragments and scFv molecules containing the light and/or heavy chain variable regions having the amino acid sequences shown in FIG. 4 and/or FIG. 6 or an amino acid sequence having at least 75%, 80%, 82%, 83%, 85%, 90%, 91%, 92%, 93%, 94%, 95%, 96%, 97%, 98% or at least 99% identity to either thereof.

In a specific embodiment, the present invention provides a specific binding molecule for use in accordance with the first aspect of the invention that is encoded by a polynucleotide having a sequence as shown in FIG. 4 and/or FIG. 6 or a polynucleotide sequence having at least 75%, 80%, 82%, 83%, 85%, 90%, 91%, 92%, 93%, 94%, 95%, 96%, 97%, 98% or at least 99% identity to either thereof.

The present invention also encompasses the use of specific binding molecules in accordance with the first aspect of the invention comprising a polypeptide having an amino acid sequence as shown in FIG. 5 and/or FIG. 7 or an amino acid sequence having at least 75%, 80%, 82%, 83%, 85%, 90%, 91%, 92%, 93%, 94%, 95%, 96%, 97%, 98% or at least 99% identity to either thereof.

In a specific embodiment, the present invention provides a specific binding molecule for use in accordance with the first aspect of the invention produced by the hybridoma cell line deposited with the European Collection of Cell Cultures (ECACC) on 3 Jun. 2010 as Accession No. 10060301.

In a second aspect, the present invention provides a pharmaceutical composition comprising a specific binding molecule as defined in relation to the first aspect of the invention for use in the treatment of obsessive compulsive disorder (OCD) or a disease related to OCD.

The pharmaceutical composition for use in accordance with this aspect of the invention can be formulated for use by any convenient route. The pharmaceutical composition for use in accordance with this aspect of the invention will normally include a pharmaceutically acceptable carrier, excipient, diluent, adjuvant, vehicle, buffer or stabiliser in addition to a specific binding molecule as defined in relation to the first aspect of the invention. Such carriers include, but are not limited to, saline, buffered saline such as phosphate buffered saline (PBS), dextrose, liposomes, water, glycerol, polyethylene glycol, ethanol and combinations thereof. This pharmaceutical composition may be in any suitable form depending upon the desired method of administering it to a patient.

It can be provided in unit dosage form, will generally be provided in a sealed container and may be provided as part of a kit. Such a kit would normally (although not necessarily) include instructions for use. It can include a plurality of said unit dosage forms.

The pharmaceutical composition can be adapted for administration by any appropriate route, for example by the oral (including buccal or sublingual), rectal, nasal, topical (including buccal, sublingual or transdermal), vaginal or parenteral (including subcutaneous, intramuscular, intravenous, intraperitoneal or intradermal) route, although it will typically be adapted for oral administration. Such compositions can be prepared by any method known in the art of pharmacy, for example by admixing the active ingredient with the carrier(s) or excipient(s) under sterile conditions.

Pharmaceutical compositions adapted for oral administration can be presented as discrete units such as capsules or tablets; as powders or granules; as solutions, syrups or suspensions (in aqueous or non-aqueous liquids; or as edible foams or whips; or as emulsions). Suitable excipients for tablets or hard gelatine capsules include lactose, maize starch or derivatives thereof, stearic acid or salts thereof. Suitable excipients for use with soft gelatine capsules include for example vegetable oils, waxes, fats, semi-solid, or liquid polyols etc. For the preparation of solutions and syrups, excipients which can be used include for example water, polyols and sugars. For the preparation of suspensions, oils (e.g. vegetable oils) can be used to provide oil-in-water or water in oil suspensions.

Pharmaceutical compositions adapted for transdermal administration can be presented as discrete patches intended to remain in intimate contact with the epidermis of the recipient for a prolonged period of time. For example, the active ingredient can be delivered from the patch by iontophoresis as generally described in *Pharmaceutical Research*, 3(6):318 (1986).

Pharmaceutical compositions adapted for topical administration can be formulated as ointments, creams, suspensions, lotions, powders, solutions, pastes, gels, sprays, aerosols or oils.

Pharmaceutical compositions adapted for rectal administration can be presented as suppositories or enemas.

Pharmaceutical compositions adapted for nasal administration wherein the carrier is a solid include a coarse powder having a particle size for example in the range 20 to 500 microns which is administered in the manner in which snuff is taken, i.e. by rapid inhalation through the nasal passage from a container of the powder held close up to the nose. Suitable compositions wherein the carrier is a liquid, for administration as a nasal spray or as nasal drops, include aqueous or oil solutions of the active ingredient.

Pharmaceutical compositions adapted for administration by inhalation include fine particle dusts or mists that can be generated by means of various types of metered dose pressurised aerosols, nebulizers or insufflators.

Pharmaceutical compositions adapted for vaginal administration can be presented as pessaries, tampons, creams, gels, pastes, foams or spray formulations.

Pharmaceutical compositions adapted for parenteral administration include aqueous and non-aqueous sterile injection solution which can contain anti-oxidants, buffers, bacteriostats and solutes which render the formulation substantially isotonic with the blood of the intended recipient; and aqueous and non-aqueous sterile suspensions which can include suspending agents and thickening agents. Excipients which can be used for injectable solutions include water, alcohols, polyols, glycerine and vegetable oils, for example. The compositions can be presented in unit-dose or multi-dose containers, for example sealed ampoules and vials, and can be stored in a freeze-dried (lyophilized) condition requiring only the addition of the sterile liquid carried, for example water for injections, immediately prior to use. Extemporaneous injection solutions and suspensions can be prepared from sterile powders, granules and tablets.

The pharmaceutical compositions can contain preserving agents, solubilising agents, stabilising agents, wetting agents, emulsifiers, sweeteners, colourants, odourants, salts, buffers, coating agents or antioxidants.

The pharmaceutical compositions for use in the invention can also contain one or more other therapeutically active agents in addition to the specific binding molecule as defined in relation to the first aspect of the present invention. In one embodiment, the pharmaceutical compositions for use in the invention contain one or more anti-inflammatory or immunomodulatory drugs in addition to the specific binding molecule as defined in relation to the first aspect of the invention. Anti-inflammatory or immunomodulatory drugs include (i) steroids such as glucocorticoids, for example prednisone, prednisolone, methylprednisolone, cortisone, hydrocortisone, betamethasone, dexamethasone and triamcinolone, (ii) non-steroidal anti-inflammatory drugs (NSAIDs) such as aspirin, ibuprofen, celecoxib and naproxen, and (iii) anti-inflammatory peptides such as Immune Selective Anti-Inflammatory Derivatives (Im-SAIDs).

Dosages of the specific binding molecule and/or pharmaceutical composition for use in the present invention can vary between wide limits, depending upon the disease or disorder to be treated, the age and condition of the individual to be treated, etc. and a physician will ultimately determine appropriate dosages to be used.

This dosage can be repeated as often as appropriate. If side effects develop the amount and/or frequency of the dosage can be reduced, in accordance with normal clinical practice.

For administration to mammals, and particularly humans, it is expected that the daily dosage of the active agent will be from 1 µg/kg to 10 mg/kg body weight, typically around 10 µg/kg to 1 mg/kg body weight. The physician in any event will determine the actual dosage which will be most suitable for an individual which will be dependent on factors including the age, weight, sex and response of the individual. The above dosages are exemplary of the average case. There can, of course, be instances where higher or lower dosages are merited, and such are within the scope of this invention.

The specific binding molecules and/or pharmaceutical compositions as defined herein are used in the treatment of obsessive compulsive disorder (OCD) or a disease related to OCD.

The invention therefore also extends to the use of a specific binding molecule as defined in relation to the first aspect of the invention or a pharmaceutical composition as defined in relation to the second aspect of the invention in the manufacture of a medicament for use in the treatment of obsessive compulsive disorder (OCD) or a disease related to OCD, or alternatively to the use of a specific binding molecule as defined in relation to the first aspect of the invention or a pharmaceutical composition as defined in relation to the second aspect of the invention in the manufacture of a medicament for the treatment of obsessive compulsive disorder (OCD) or a disease related to OCD.

The invention also includes a method for the treatment of obsessive compulsive disorder (OCD) or a disease related to OCD in a subject, typically a subject in need thereof, comprising administering to the subject a specific binding molecule as defined in relation to the first aspect of the invention or a pharmaceutical composition as defined in relation to the second aspect of the invention. The method of treatment can be of a human or an animal subject and the invention extends equally to uses in both human and/or veterinary medicine. The specific binding molecule and/or pharmaceutical composition for use in the invention is preferably administered to an individual in a "therapeutically effective amount", this being sufficient to show benefit to the individual and/or to ameliorate, eliminate or prevent one or more symptoms of OCD or a related disease. As used herein, "treatment" includes any regime that can benefit a human or non-human animal, preferably a mammal. The treatment may be in respect of an existing condition or may be prophylactic (preventative treatment).

By "a disease related to OCD", used herein in relation to all aspects of the invention, is typically meant any one or more of the following diseases: trichotillomania, dermatillomania, Tourette's Syndrome (TS), Asperger's syndrome, anorexia, bulimia, depression, panic disorder, panic attacks, bipolar disorder, hypochondriasis, post-traumatic stress disorder (PTSD), social anxiety disorder, schizophrenia, attention deficit hyperactivity disorder (ADHD) and body dysmorphic disorder (BDD).

Preferred features for the second and subsequent aspects of the invention are as for the first aspect mutatis mutandis.

In one embodiment, the present invention provides a specific binding molecule raised against the full-length human Anx-A1 protein having the amino acid sequence shown in FIG. 2A for use in the treatment of obsessive compulsive disorder (OCD) or a disease related to OCD. One example of such a specific binding molecule is the monoclonal antibody VJ-4B6 produced by the hybridoma cell line deposited with the European Collection of Cell Cultures (ECACC) on 3 Jun. 2010 as Accession No. 10060301.

In one embodiment, the present invention provides a specific binding molecule having the CDRs of the monoclonal antibody VJ-4B6, which have the following amino acid sequences:

```
                                        (SEQ ID NO: 2)
VLCDR1 is KASENVVTYVS (SEQ ID NO: 3)
VLCDR2 is GASNRYT (SEQ ID NO: 4)
VLCDR3 is GQGYSYPYT (SEQ ID NO: 5)
VHCDR1 is GYTFTNYWIG (SEQ ID NO: 6)
VHCDR2 is DIYPGGDYTNYNEKFKG (SEQ ID NO: 7)
VHCDR3 is WGLGYYFDY
``` for use in the treatment of OCD or a disease related to OCD.

In one specific embodiment, the present invention provides a specific binding molecule having the $V_L$ and/or $V_H$ regions of the monoclonal antibody VJ-4136, which are shown in FIGS. 4 and 6 respectively for use in the treatment of OCD. In one embodiment, the monoclonal antibody VJ-4B6 is diluted in phosphate buffered saline (PBS) prior to administration. In one embodiment, the monoclonal antibody VJ-4B6 is administered intraperitoneally.

The present invention will now be further described by way of reference to the following Examples which are present for the purposes of illustration only. In the Examples, reference is made to a number of Figures in which:

FIG. 1A is a ribbon diagram of annexin-1 structure showing the four annexin repeats and the N-terminal domain. FIG. 1B is a schematic representation of the annexin repeats and the location of the bioactive sequence, Annexin-1 peptide Ac.2-26. FIG. 1C shows the amino acid sequence of peptide Ac.2-26 (SEQ ID NO:1), which is an acetylated N-terminal peptide fragment of Anx-A1.

FIG. 2A shows (i) the amino acid sequence (SEQ ID NO:8) and (ii) the nucleotide sequence (SEQ ID NO:9) of human Annexin-1 (Anx-A1), isoform ANXA1-003. FIG. 2B shows the amino acid sequence (SEQ ID NO:10) of human Annexin-1 (Anx-A1), isoform ANXA1-002. FIG. 2C shows the amino acid sequence SEQ ID NO:11) of human Annexin-1(Anx-A1), isoform ANXA1-004. FIG. 2D shows the amino acid sequence (SEQ ID NO:12) of human Annexin-1 (Anx-A1), isoform ANXA1-006.

FIGS. 3A and 3B show the generation of VJ-4B6. (A) Schematic representation of the strategy used to isolate and produce VJ-4B6. (B) The histogram shows the staining of cell lines stably transfected with Annexin-1 cDNA (green line; right-hand peak) or an irrelevant control cDNA (red line; left-hand peak) with VJ-4B6.

FIG. 5 shows the amino acid sequence (SEQ ID NO:16) of the light chain variable region of VJ-4B6 with the CDRs annotated. CDR1, CDR2, CDR3 and the beginning of the constant region are highlighted. Numbering and CDRs according to Kabat.

Figure 6:
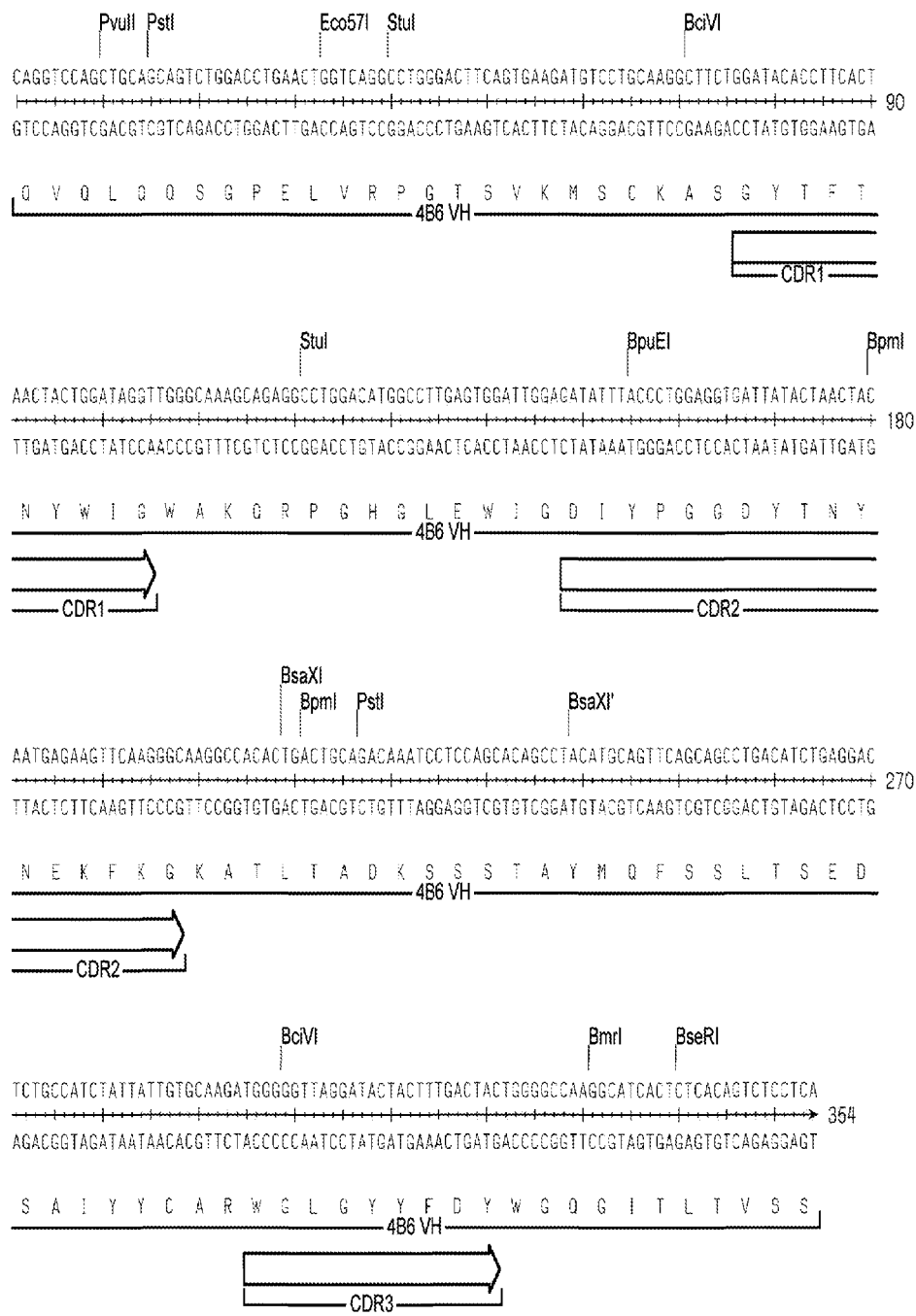

FIG. 6 shows the DNA (SEQ ID NO:17) and amino acid sequence (SEQ ID NO:19) of the heavy chain variable region of VJ-4B6, and the anti-sense of heavy chain variable region of VJ-4B6 (SEQ ID NO:18).

FIG. 7 shows the amino acid sequence (SEQ ID NO:20) of the heavy chain variable region of VJ-4B6 with the CDRs annotated. CDR1, CDR2, CDR3 and the beginning of the constant region are highlighted. Numbering and CDRs according to Kabat. In the heavy chain variable region residues 26 to 29, although not part of the hypervariable region as defined by Kabat, are part of the CDR loop defined by Chothia (Chothia and Lesk, 1987). Positions at insertions 52, 52a, 82, 82a, 82b, 82c, 100 and 100a, are indicated as 52a, 82abc, 100a.

Figure 8A:
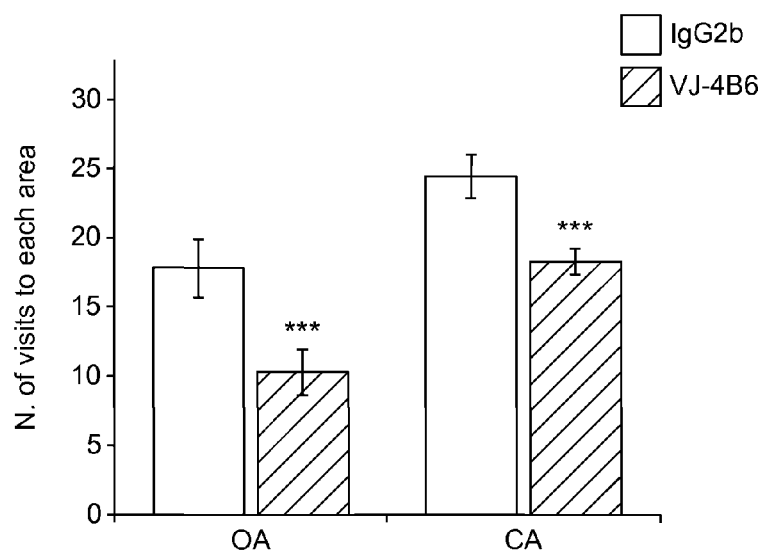
Figure 8B:
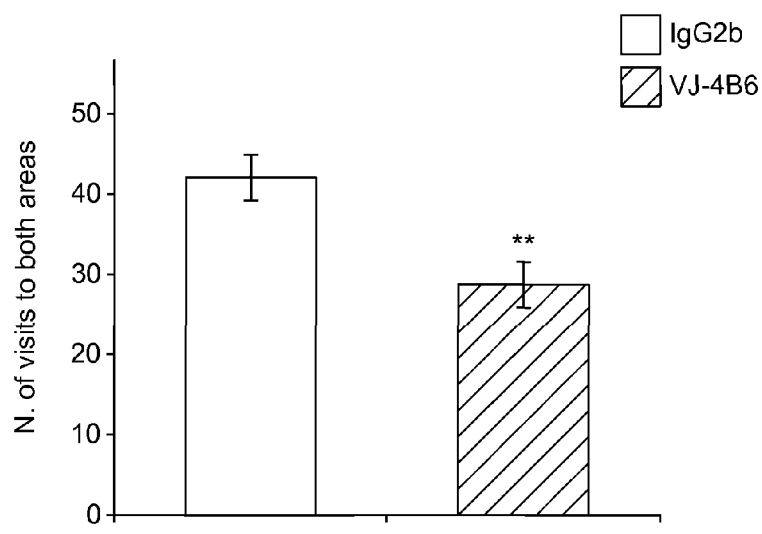

FIGS. 8A and 8B show the effect VJ-4B6 on anxiety. Male (n=6) C57/BL6 mice (5-6 week age) received an i.p. injection of VJ-4B6 (100 ng/100 ml) or IgG2b control (100 ng/100 ml). Six days later mice were tested with the elevated plus maze. The graph in A shows the number of entries in the open (OA) or closed (CA) arm of the maze while the graph in B shows the cumulative (OA+CA) results of the test. number of entries. * $P<0.001$;  $P<0.005$ vs. IgG control.

Figure 9A:
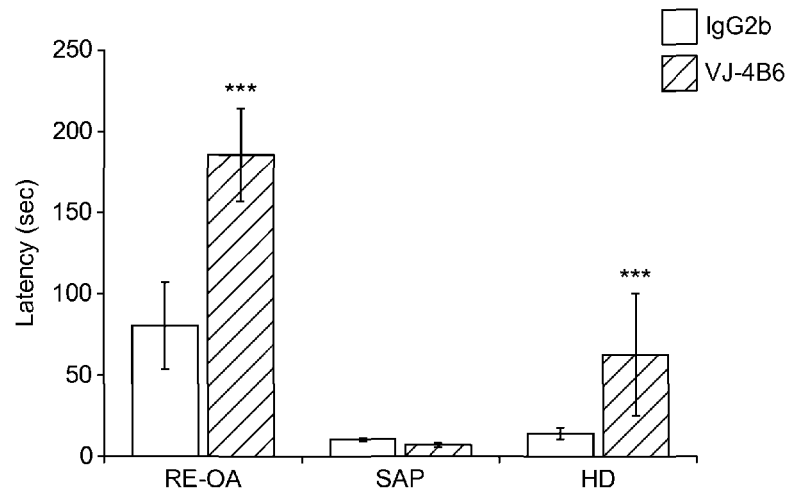
Figure 9B:
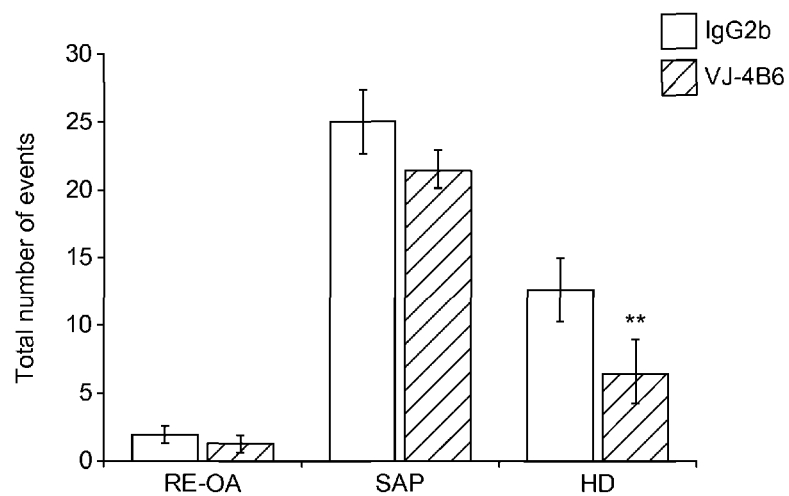

FIGS. 9A and 9B show the effect of VJ-4B6 on risk assessment behavior. Male (n=6) C57/BL6 mice (5-6 week age) received an i.p. injection of VJ-4B6 (100 ng/100 ml) or IgG2b (100 ng/100 ml). Six days later mice were tested with the elevated plus maze. The graph in A shows the latency to: reach end open arm (RE-OA), stretch attend posture (SAP), head dips (HD) while the graph in B shows the total number of events for each specific activity. * $P<0.001$;  $P<0.005$ vs. IgG control.

Figure 10A:
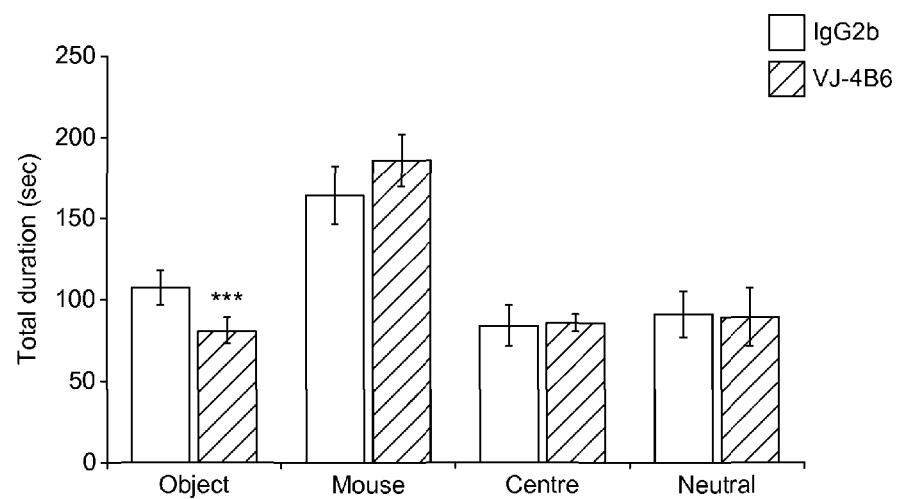
Figure 10B:
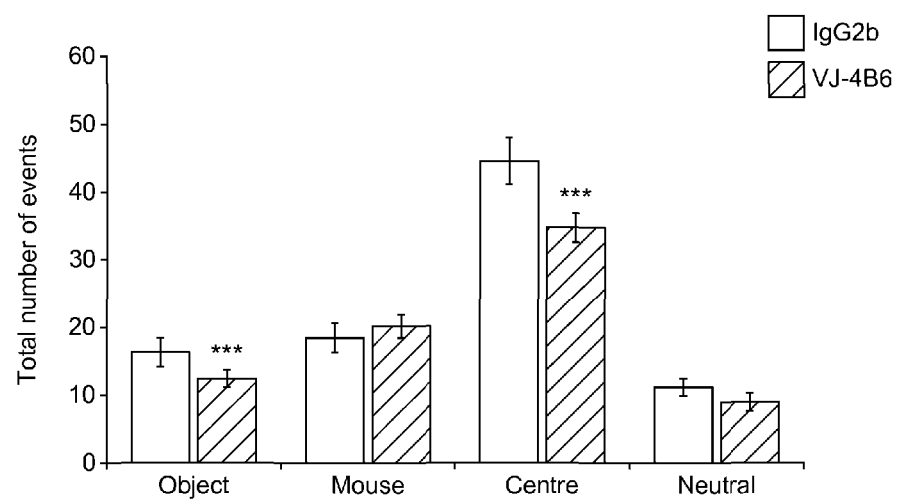

FIGS. 10A and 10B show the effect of VJ-4B6 on social interaction. Male (n=6) C57/BL6 mice (5-6 week age) received an i.p. injection of VJ-4B6(100 ng/100ml) or IgG2b (100 ng/100 ml). Six days later mice were tested with the Y-maze social interaction test. The graph in A shows the total duration of interaction with an object, a mouse as well as the time spent at the centre of the Y-maze or in neutral position. The graph in B shows the total number of events for each specific activity. * $P<0.001$;  $P<0.005$ vs. IgG control.

Figure 11A:
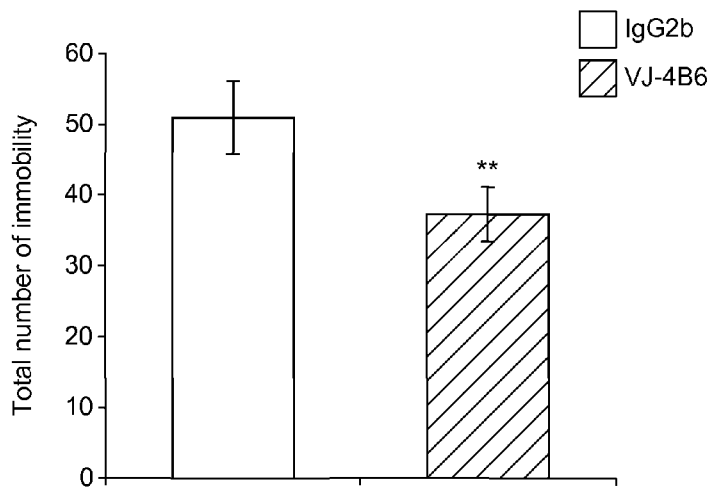
Figure 11B:
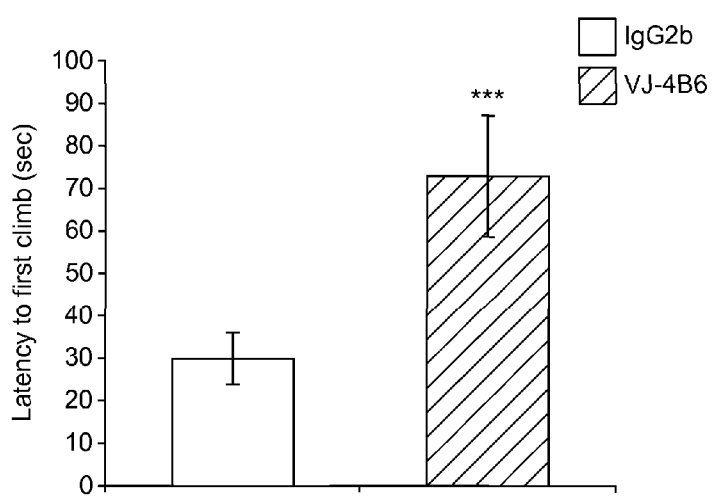

FIGS. 11A and 11B show the effect of VJ-4B6 on depression and despair. Male (n=6) C57/BL6 mice (5-6 week age) received an i.p. injection of VJ-4B6 (100 ng/100 ml) or IgG2b (100 ng/100 ml). Six days later mice were tested with the tail suspension test. The graph in A shows the number of immobility while the graph in B shows the time in seconds till the first climbing event. * $P<0.001$;  $P<0.005$ vs. IgG control.

Figure 12A:
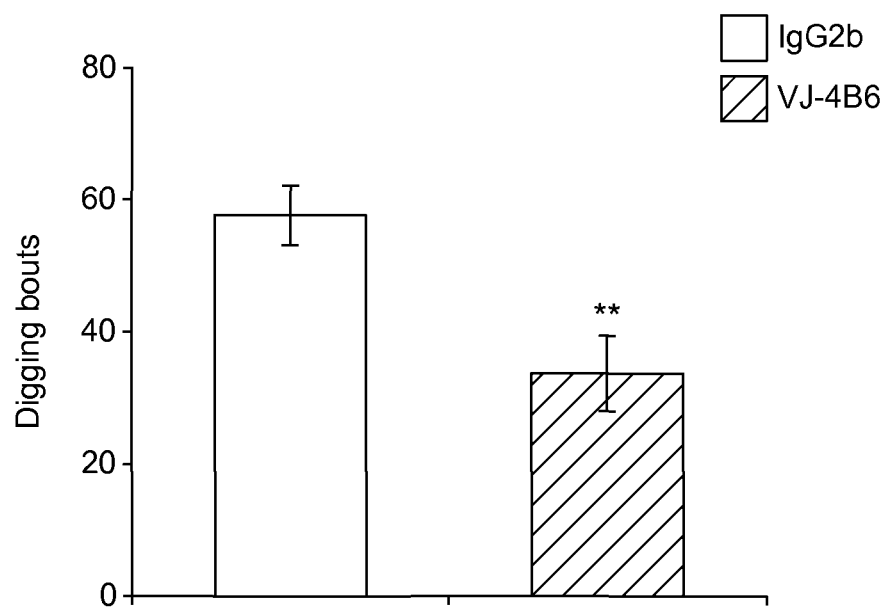
Figure 12B:
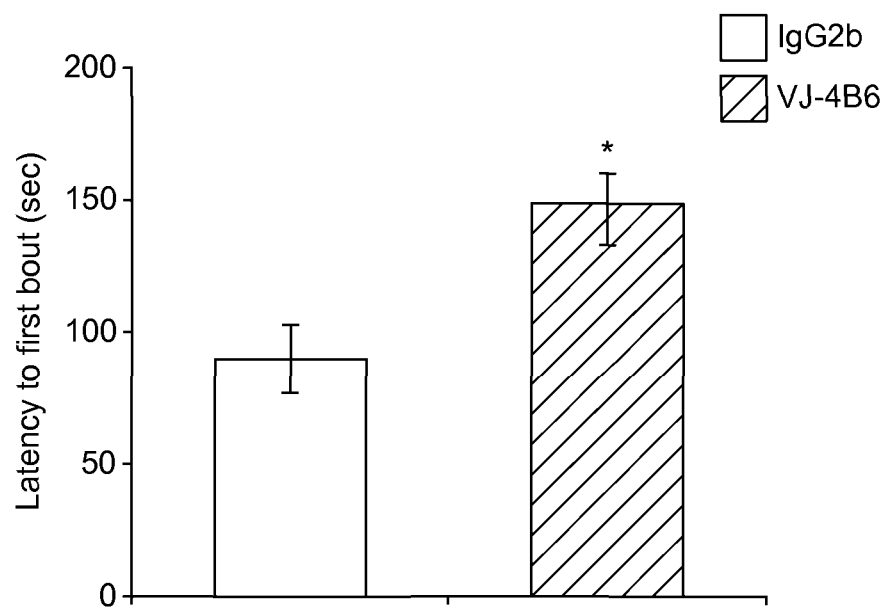

FIGS. 12A and 12B show the effect of VJ-4B6 on digging behavior. Male (n=6) C57/BL6 mice (5-6 week age) received an i.p. injection of VJ-4B6(100 ng/100 ml) or IgG2b (100 ng/100 ml). Six days later mice were tested for digging behavior. The graph in A shows the number of bouts while the graph in B shows the time in seconds till the first digging event. ** $P<0.005$; * $P<0.05$ vs. IgG control.

Figure 13:
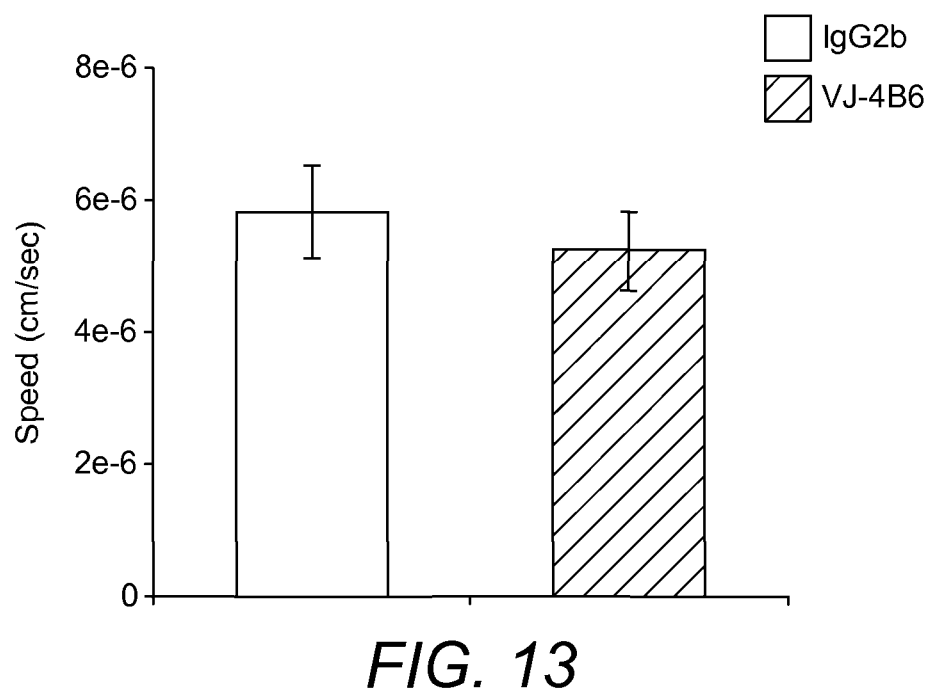

FIG. 13 shows the effect of VJ-4B6 on motor activity. Male (n=6) C57/BL6 mice (5-6 week age) received an i.p. injection of VJ-4B6 (100 ng/100 ml) or IgG2b (100 ng/100 ml). Six days later mice were tested with the rotarod performance test. The graph shows the average speed of the mice after treatment.

EXAMPLE 1

Production of Antibody VJ-4B6

Figure 3B:
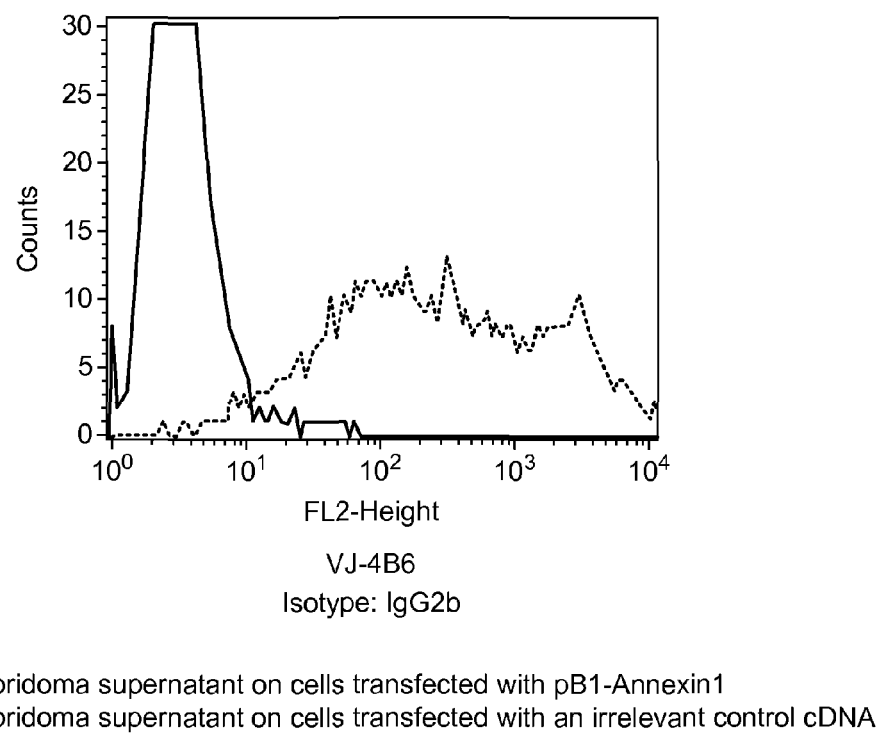

A novel anti-AnxA1 antibody was generated by genetic immunisation as indicated in the scheme in FIG. 3A (Genovac GmbH, Germany). Serum from several immunized mice were tested and three resulted positive for IgG recognizing cells transfected with AnxA1 cDNA. Splenocytes from these mice were fused to myeloma cells to generate hybridoma cells. Only one of the three hybridoma cell clones were successfully subcloned and expanded. These hybridoma cells are called VJ-4B6-E5-B10-D4. Purified IgG2b fraction from the hybridoma cells recognizes cells transfected with AnxA1 cDNA (FIG. 3B, green line; right-hand peak) but not cell transfected with an irrelevant cDNA (FIG. 3B, red line; left-hand peak).

EXAMPLE 2

Sequencing of VJ-4B6

The aim of this Example was to clone the antibody heavy and light chain variable region genes from the hybridoma cells and to determine the DNA sequence and location of the complementarity determining regions (CDRs) and other features.

Cloning and Sequencing of Antibody Variable Regions

Total RNA was prepared from 1 vial of hybridoma cells using the Qiagen RNeasy mini kit (Cat No: 74104). RNA was eluted in 50 μL water and checked on a 1.2% agarose gel.

$V_H$ and $V_K$ (variable kappa light chain) cDNAs were prepared using reverse transcriptase with IgG and kappa constant region primers. The first strand cDNAs were amplified by PCR using a large set of signal sequence primers. The amplified DNAs were gel-purified and cloned into the vector pGem® T Easy (Promega). The $V_H$ and $V_K$ clones obtained were screened for inserts of the expected size. The DNA sequence of selected clones was determined in both directions by automated DNA sequencing. The locations of the complementarity determining regions (CDRs) in the sequences were determined with reference to other antibody sequences (Kabat E A et al., 1991).

Results

VJ-4B6 Light Chain

Figure 4:
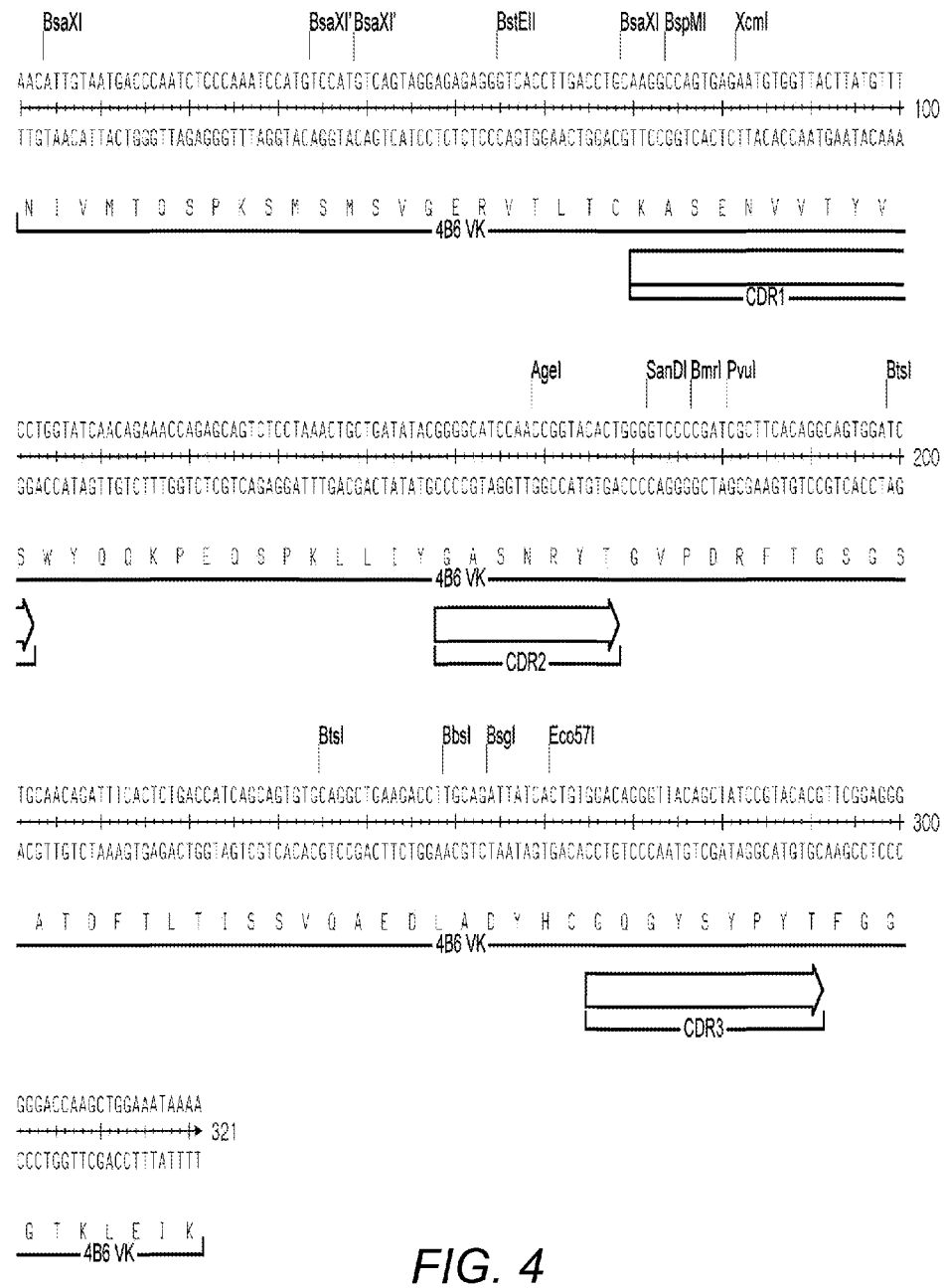
FIG. 4 shows the DNA (SEQ ID NO:13) and amino acid sequence (SEQ ID NO:15) of the light chain variable region of VJ-4B6, and the anti-sense of light chain variable region of VJ-4B6 (SEQ ID NO:14).

A single $V_K$ sequence was identified. The DNA sequence and deduced amino acid sequence for the VJ-4B6 $V_K$ is shown in FIG. 4. The deduced protein sequence with CDRs annotated is shown in FIG. 5. Nine clones (seven independent) from two separate amplification steps gave identical V region sequence. The non-productive aberrant $V_K$ sequence that arises from the hybridoma fusion partner was also present in a number of clones and there was one clone with a deletion within the sequence.

VJ-4B6 Heavy Chain

A single $V_H$ sequence was identified. The DNA sequence and deduced amino acid sequence for the VJ-4B6 $V_H$ is shown in FIG. 6. The same V region sequence was found in nine independent clones. Two clones had a single base pair change, one clone had a single base pair deletion and a single base pair change, and one clone had two single base pair changes. Each of the five single base pair changes occurred in only one clone. The remaining five clones had identical sequence. The deduced protein sequence with CDRs annotated is shown in FIG. 7.

REFERENCES

Chothia C and Lesk A M. Canonical structures for the hypervariable regions of immunoglobulins. J Mol Biol. 196: 901-17, 1987.

Kabat E A, Wu T T, Perry H M, Gottesman K S, Foeller C. Sequences of proteins of Immunological Interest, US Department of Health and Human Services, 1991

EXAMPLE 3

Effects of VJ-4B6 on Mouse Model of Obsessive Compulsive Disorder (OCD) In Vivo The present inventors have developed a transgenic mouse model of obsessive compulsive disorder in which Anx-A1 is overexpressed in T cells. This is the subject of co-pending UK patent application no. 1121561.3 which was filed on the same day as the present application.

Transgenic mice overexpressing Anx-A1 (Anx-A1$^{tg}$) in T cells were generated by inserting C-terminus FLAG-tagged Anx-A1 into the mouse genome using a VACD2 cassette vector and the technique of pronuclear microinjection. Briefly, the murine Anx-A1 gene was amplified and tagged with the FLAG epitope and then cloned into the pcDNA3.1 vector. The Anx-A1 FLAG was recovered from the pcDNA3.1 vector and then ligated into linearised VACD2 vector. The VACD2 Anx-A1 FLAG construct was then modified and purified, then inserted into the mouse genome by pronuclear injection. These mice were used in the present Example as follows.

Mice received an intraperitoneal injection of VJ-4B6 or control IgG in phosphate buffered saline (PBS). Six days later mice were tested as detailed below.

FIGS. 8 and 9. Elevated Plus Maze Test

Background. The elevated plus maze test is one of the most widely used tests for measuring anxiety-like behavior. The test is based on the natural aversion of mice for open and elevated areas, as well as on their natural spontaneous exploratory behavior in novel environments. The apparatus consists of open arms and closed arms, crossed in the middle perpendicularly to each other, and a center area. Mice are given access to all of the arms and are allowed to move freely between them. The number of entries into the open arms and the time spent in the open arms are used as indices of open space-induced anxiety in mice.

Test. Each mouse was placed in the central square of the maze (5 cm×5 cm), facing one of the closed arms. Mouse behavior was recorded during a 10-min test period. The number of entries into, and the time spent on open and closed arms were recorded. Data acquisition and analysis were performed automatically using Image EP software.

Stretch-attended postures and head dips were recorded as measures of risk-assessment behaviors, which are more sensitive measures of anxiety on the elevated plus maze than Open Arm Time (Rodgers, R J, Cole, J C, Physiol Behav 53: 383-388 (1993); Rodgers R J, Haller J, Holmes A, Halasz J, Walton T J, Brain P F, Physiology & Behavior 68: 47-53 (1999)). A stretch-attended posture was a posture where the mice stretched forward to its full body length without moving the hind limbs and then returned to its original position. A head dip occurred when the mice stretched its head and shoulders over the edge of the maze and looked down to the floor.

Results. FIGS. 8 and 9 show that mice treated with VJ-4B6 are less anxious regardless of the type of fearful condition—this being very fearful (open arm) or less fearful (closed arm). They also "enjoy the run of life" (increased reach end open arm) and more curious/adventurous (increased head dips) because of less anxiety.

FIG. 10. Y Maze.

Background. Y-Maze is a behavioral test used to assess memory function and the willingness of rodents to explore new environments. The Y-Maze is particularly useful in evaluating the effects of drugs on cognition. As mice and rats typically prefer to explore a new arm of the maze rather than returning to one that was previously visited, the data is analyzed to determine the number of arm entries without repetition. Normal (control) animals will reflect a high rate of alternation which indicates that the animal can remember which arm was entered last. The Y-Maze can also be used for social interaction test to determine whether a mouse prefers to spend time with a novel or known object or mouse.

Test. The test apparatus used is a Y-shaped maze with three identical arms at a 120° angle from each other. Gradual turns of the Y-Maze decrease learning time as compared to the sharp turns of the T-maze. The animal is placed in the centre of the Y maze, and the total number of individual arm entries as well as the sequence of entries is recorded Results. FIG. 10 shows that treatment with VJ-4B6 makes mice "smarter" since they spend less time with an unanimated object while maintaining the same attention to animated stimuli (another mouse). They are also more sociable and friendly since they go through the centre of the Y maze less and hence spend more time in the arms.

FIG. 11. Tail Suspension Test.

Background. The TST is based on the observation that rodents, after initial escape-oriented movements, develop an immobile posture when placed in an inescapable stressful situation. In the case of the TST the stressful situation involves the haemodynamic stress of being hung in an uncontrollable fashion by their tail. If antidepressant treatments are given prior to the test, the subjects will actively persist engaging in escape-directed behaviours for longer periods of time.

Test. On the day of test mice were transferred to the experiment room and allowed to acclimatize for 1 h. An automated tail-suspension apparatus with a tail hanger connected to a precision linear load cell was used. In all, 1 cm of the mouse's tail was inserted into the tail hanger and secured with nonirritating adhesive tape. Mice remained suspended by the tail, at a height of 35 cm from the tabletop, for 6 min. During this time the load cell recorded the mouse's movements and transmitted the information to a central computer, which then recorded the rate of immobility within the course of the session, and calculated total duration of immobility. Decreased levels of immobility are highly predictive of antidepressant efficacy (Cryan et al, Neurosci Biobehav Rev 29(4-5): 571-625 (2005)).

Results. Administration of VJ-4B6 makes mice less despaired because they fight the stressful situation (tail suspension) more by being more mobile (FIG. 11A). At the same time they are more patient since it takes more time until they try to fight the stressful situation by clubbing on their tail (FIG. 11B).

FIG. 12. Marble Burying and Digging Behavior Test.

Background. These tests measures anxiety-related behaviour of the mouse. Over the last decades, the suppression of digging and spontaneous burying of glass marbles by mice has been used as an index of anxiolytic drug action, i.e., in the marble burying and digging tests, acute administration of benzodiazepines and different classes of antidepressants inhibit digging and marble burying.

Test. On the day of test mice were transferred to the experiment room and allowed to acclimatize for 1 h. Each mouse was placed in a plastic cage (approximately 20×30 cm) with fifteen glass marbles were placed evenly spaced in 5 rows of 3 onto a 5 cm layer of sawdust bedding, lightly pressed down to make a flat even surface. Measurements included the latency to start digging and the number of individual digging bouts. Test duration was 15 min.

Results. The results in FIG. 12A show that administration of VJ-4136 to mice reduced the number of bouts compared to control IgG2b-treated animals in the marble burying test suggesting an anxiolytic effect of the antibody. Consistent with this hypothesis, the latency to the first bout (another index of anxious behaviour) was also significantly higher.

FIG. 13. Rotarod.

Background. The Rotarod Performance test is a performance test based on a rotating rod with forced motor activity being applied, usually by a rodent. The accelerating rotarod, where a rotating rod or drum functions as a treadmill for the rodent placed atop, is widely used to assess drug and genetic effects on motor coordination in rodents.

Test. On the day of test mice were transferred to the experiment room and allowed to acclimatize for 1 h. Each mouse was placed on a stationary rod that begins to rotate with a smooth increase in speed from 5 rpm to 70 rpm over 3 min. The speed required to fall off the rotarod was recorded.

Results. The results of these test show that the effects shown in the earlier tests are not unspecific or due to general impairment of cognitive or motor function since treatment with VJ-4B6 has no effect on the rotarod test.

SUMMARY

These results show that antibodies that bind to Anx-A1, such as the antibody VJ-4B6, are useful in the treatment of OCD and related disorders such as depression.

The invention claimed is:

1. A method for the treatment of obsessive compulsive disorder (OCD) or anxiety in a subject in need thereof, comprising administering to the subject an antibody or fragment thereof that binds human Annexin-1 (Anx-A1) having the amino acid sequence of SEQ ID NO:8, comprising Complementarity Determining Regions (CDRs) VLCDR1, VLCDR2, VLCDR3, VHCDR1, VHCDR2 and VHCDR3, wherein each of VLCDR1, VLCDR2, VLCDR3, VHCDR1, VHCDR2, and VHCDR3 corresponds to VLCDR1, VLCDR2, VLCDR3, VHCDR1, VHCDR2, and VHCDR3, respectively, of an antibody produced by the hybridoma cell line deposited with the European Collection of Cell Cultures (ECACC) on 3 Jun. 2010 as Accession No. 10060301.

2. The method according to claim 1 wherein the antibody is a monoclonal antibody.

3. The method according to claim 2 wherein the monoclonal antibody is humanized.

4. The method according to claim 1 wherein the fragment is a Fab, F(ab')$_2$ or Fv fragment or an scFv molecule.

5. The method according to claim 1 wherein the antibody or fragment thereof comprises a polypeptide comprising SEQ ID NO:19.

6. The method according to claim 1 wherein the antibody or fragment thereof comprises a light chain variable region and a heavy chain variable region each of which is produced by the hybridoma cell line deposited with the European Collection of Cell Cultures (ECACC) on 3 Jun. 2010 as Accession No. 10060301, or a humanized antibody or fragment thereof.

7. The method according to claim 1 wherein the antibody or fragment thereof is present within a pharmaceutical composition.

8. The method according to claim 7 wherein the pharmaceutical composition comprises another therapeutically active agent.

* * * * *

SEQUENCE LISTING

```
<160> NUMBER OF SEQ ID NOS: 20

<210> SEQ ID NO 1
<211> LENGTH: 25
<212> TYPE: PRT
<213> ORGANISM: Homo sapiens
<220> FEATURE:
<221> NAME/KEY: ACETYLATION
<222> LOCATION: (1)..(1)

<400> SEQUENCE: 1

Ala Met Val Ser Glu Phe Leu Lys Gln Ala Trp Phe Ile Glu Asn Glu
```

```
1               5                   10                  15
Glu Gln Glu Tyr Val Gln Thr Val Lys
            20                  25

<210> SEQ ID NO 2
<211> LENGTH: 11
<212> TYPE: PRT
<213> ORGANISM: Unknown
<220> FEATURE:
<223> OTHER INFORMATION: VLCDR1

<400> SEQUENCE: 2

Lys Ala Ser Glu Asn Val Val Thr Tyr Val Ser
1               5                   10

<210> SEQ ID NO 3
<211> LENGTH: 7
<212> TYPE: PRT
<213> ORGANISM: Unknown
<220> FEATURE:
<223> OTHER INFORMATION: VLCDR2

<400> SEQUENCE: 3

Gly Ala Ser Asn Arg Tyr Thr
1               5

<210> SEQ ID NO 4
<211> LENGTH: 9
<212> TYPE: PRT
<213> ORGANISM: Unknown
<220> FEATURE:
<223> OTHER INFORMATION: VLCDR3

<400> SEQUENCE: 4

Gly Gln Gly Tyr Ser Tyr Pro Tyr Thr
1               5

<210> SEQ ID NO 5
<211> LENGTH: 10
<212> TYPE: PRT
<213> ORGANISM: Unknown
<220> FEATURE:
<223> OTHER INFORMATION: VHCDR1

<400> SEQUENCE: 5

Gly Tyr Thr Phe Thr Asn Tyr Trp Ile Gly
1               5                   10

<210> SEQ ID NO 6
<211> LENGTH: 17
<212> TYPE: PRT
<213> ORGANISM: Unknown
<220> FEATURE:
<223> OTHER INFORMATION: VHCDR2

<400> SEQUENCE: 6

Asp Ile Tyr Pro Gly Gly Asp Tyr Thr Asn Tyr Asn Glu Lys Phe Lys
1               5                   10                  15
Gly

<210> SEQ ID NO 7
<211> LENGTH: 9
<212> TYPE: PRT
<213> ORGANISM: Unknown
<220> FEATURE:
<223> OTHER INFORMATION: VHCDR3
```

<400> SEQUENCE: 7

Trp Gly Leu Gly Tyr Tyr Phe Asp Tyr
1               5

<210> SEQ ID NO 8
<211> LENGTH: 346
<212> TYPE: PRT
<213> ORGANISM: Homo sapiens

<400> SEQUENCE: 8

Met Ala Met Val Ser Glu Phe Leu Lys Gln Ala Trp Phe Ile Glu Asn
1               5                   10                  15

Glu Glu Gln Glu Tyr Val Gln Thr Val Lys Ser Ser Lys Gly Gly Pro
                20                  25                  30

Gly Ser Ala Val Ser Pro Tyr Pro Thr Phe Asn Pro Ser Ser Asp Val
            35                  40                  45

Ala Ala Leu His Lys Ala Ile Met Val Lys Gly Val Asp Glu Ala Thr
        50                  55                  60

Ile Ile Asp Ile Leu Thr Lys Arg Asn Asn Ala Gln Arg Gln Gln Ile
65                  70                  75                  80

Lys Ala Ala Tyr Leu Gln Glu Thr Gly Lys Pro Leu Asp Glu Thr Leu
                85                  90                  95

Lys Lys Ala Leu Thr Gly His Leu Glu Glu Val Val Leu Ala Leu Leu
            100                 105                 110

Lys Thr Pro Ala Gln Phe Asp Ala Asp Glu Leu Arg Ala Ala Met Lys
        115                 120                 125

Gly Leu Gly Thr Asp Glu Asp Thr Leu Ile Glu Ile Leu Ala Ser Arg
130                 135                 140

Thr Asn Lys Glu Ile Arg Asp Ile Asn Arg Val Tyr Arg Glu Glu Leu
145                 150                 155                 160

Lys Arg Asp Leu Ala Lys Asp Ile Thr Ser Asp Thr Ser Gly Asp Phe
                165                 170                 175

Arg Asn Ala Leu Leu Ser Leu Ala Lys Gly Asp Arg Ser Glu Asp Phe
            180                 185                 190

Gly Val Asn Glu Asp Leu Ala Asp Ser Asp Ala Arg Ala Leu Tyr Glu
        195                 200                 205

Ala Gly Glu Arg Arg Lys Gly Thr Asp Val Asn Val Phe Asn Thr Ile
    210                 215                 220

Leu Thr Thr Arg Ser Tyr Pro Gln Leu Arg Arg Val Phe Gln Lys Tyr
225                 230                 235                 240

Thr Lys Tyr Ser Lys His Asp Met Asn Lys Val Leu Asp Leu Glu Leu
                245                 250                 255

Lys Gly Asp Ile Glu Lys Cys Leu Thr Ala Ile Val Lys Cys Ala Thr
            260                 265                 270

Ser Lys Pro Ala Phe Phe Ala Glu Lys Leu His Gln Ala Met Lys Gly
        275                 280                 285

Val Gly Thr Arg His Lys Ala Leu Ile Arg Ile Met Val Ser Arg Ser
    290                 295                 300

Glu Ile Asp Met Asn Asp Ile Lys Ala Phe Tyr Gln Lys Met Tyr Gly
305                 310                 315                 320

Ile Ser Leu Cys Gln Ala Ile Leu Asp Glu Thr Lys Gly Asp Tyr Glu
                325                 330                 335

Lys Ile Leu Val Ala Leu Cys Gly Gly Asn
            340                 345

<210> SEQ ID NO 9
<211> LENGTH: 1041
<212> TYPE: DNA
<213> ORGANISM: Homo sapiens

<400> SEQUENCE: 9

```
atggcaatgg tatcagaatt cctcaagcag gcctggttta ttgaaaatga agagcaggaa      60
tatgttcaaa ctgtgaagtc atccaaaggt ggtcccggat cagcggtgag cccctatcct     120
accttcaatc catcctcgga tgtcgctgcc ttgcataagg ccataatggt taaaggtgtg     180
gatgaagcaa ccatcattga cattctaact aagcgaaaca atgcacagcg tcaacagatc     240
aaagcagcat atctccagga aacaggaaag cccctggatg aaacactgaa gaaagccctt     300
acaggtcacc ttgaggaggt tgttttggct ctgctaaaaa ctccagcgca atttgatgct     360
gatgaacttc gtgctgccat gaagggcctt ggaactgatg aagatactct aattgagatt     420
ttggcatcaa gaactaacaa agaaatcaga gacattaaca gggtctacag agaggaactg     480
aagagagatc tggccaaaga cataacctca gacacatctg agattttcg gaacgctttg     540
ctttctcttg ctaagggtga ccgatctgag gactttggtg tgaatgaaga cttggctgat     600
tcagatgcca gggccttgta tgaagcagga gaaaggagaa aggggacaga cgtaaacgtg     660
ttcaatacca tccttaccac cagaagctat ccacaacttc gcagagtgtt tcagaaatac     720
accaagtaca gtaagcatga catgaacaaa gttctggacc tggagttgaa aggtgacatt     780
gagaaatgcc tcacagctat cgtgaagtgc gccacaagca aaccagcttt ctttgcagag     840
aagcttcatc aagccatgaa aggtgttgga actcgccata aggcattgat caggattatg     900
gtttcccgtt ctgaaattga catgaatgat atcaaagcat tctatcagaa gatgtatggt     960
atctcccttt gccaagccat cctggatgaa accaaaggag attatgagaa aatcctggtg    1020
gctctttgtg gaggaaacta a                                               1041
```

<210> SEQ ID NO 10
<211> LENGTH: 346
<212> TYPE: PRT
<213> ORGANISM: Homo sapiens

<400> SEQUENCE: 10

```
Met Ala Met Val Ser Glu Phe Leu Lys Gln Ala Trp Phe Ile Glu Asn
 1               5                  10                  15

Glu Glu Gln Glu Tyr Val Gln Thr Val Lys Ser Ser Lys Gly Gly Pro
            20                  25                  30

Gly Ser Ala Val Ser Pro Tyr Pro Thr Phe Asn Pro Ser Ser Asp Val
        35                  40                  45

Ala Ala Leu His Lys Ala Ile Met Val Lys Gly Val Asp Glu Ala Thr
    50                  55                  60

Ile Ile Asp Ile Leu Thr Lys Arg Asn Asn Ala Gln Arg Gln Gln Ile
65                  70                  75                  80

Lys Ala Ala Tyr Leu Gln Glu Thr Gly Lys Pro Leu Asp Glu Thr Leu
                85                  90                  95

Lys Lys Ala Leu Thr Gly His Leu Glu Glu Val Val Leu Ala Leu Leu
           100                 105                 110

Lys Thr Pro Ala Gln Phe Asp Ala Asp Glu Leu Arg Ala Ala Met Lys
       115                 120                 125

Gly Leu Gly Thr Asp Glu Asp Thr Leu Ile Glu Ile Leu Ala Ser Arg
   130                 135                 140
```

-continued

Thr Asn Lys Glu Ile Arg Asp Ile Asn Arg Val Tyr Arg Glu Glu Leu
145                 150                 155                 160

Lys Arg Asp Leu Ala Lys Asp Ile Thr Ser Asp Thr Ser Gly Asp Phe
                165                 170                 175

Arg Asn Ala Leu Leu Ser Leu Ala Lys Gly Asp Arg Ser Glu Asp Phe
            180                 185                 190

Gly Val Asn Glu Asp Leu Ala Asp Ser Asp Ala Arg Ala Leu Tyr Glu
        195                 200                 205

Ala Gly Glu Arg Arg Lys Gly Thr Asp Val Asn Val Phe Asn Thr Ile
210                 215                 220

Leu Thr Thr Arg Ser Tyr Pro Gln Leu Arg Arg Val Phe Gln Lys Tyr
225                 230                 235                 240

Thr Lys Tyr Ser Lys His Asp Met Asn Lys Val Leu Asp Leu Glu Leu
                245                 250                 255

Lys Gly Asp Ile Glu Lys Cys Leu Thr Ala Ile Val Lys Cys Ala Thr
            260                 265                 270

Ser Lys Pro Ala Phe Phe Ala Glu Lys Leu His Gln Ala Met Lys Gly
        275                 280                 285

Val Gly Thr Arg His Lys Ala Leu Ile Arg Ile Met Val Ser Arg Ser
    290                 295                 300

Glu Ile Asp Met Asn Asp Ile Lys Ala Phe Tyr Gln Lys Met Tyr Gly
305                 310                 315                 320

Ile Ser Leu Cys Gln Ala Ile Leu Asp Glu Thr Lys Gly Asp Tyr Glu
                325                 330                 335

Lys Ile Leu Val Ala Leu Cys Gly Gly Asn
            340                 345

<210> SEQ ID NO 11
<211> LENGTH: 204
<212> TYPE: PRT
<213> ORGANISM: Homo sapiens

<400> SEQUENCE: 11

Met Asn Leu Ile Leu Arg Tyr Thr Phe Ser Lys Met Ala Met Val Ser
1               5                   10                  15

Glu Phe Leu Lys Gln Ala Trp Phe Ile Glu Asn Glu Glu Gln Glu Tyr
                20                  25                  30

Val Gln Thr Val Lys Ser Ser Lys Gly Gly Pro Gly Ser Ala Val Ser
            35                  40                  45

Pro Tyr Pro Thr Phe Asn Pro Ser Ser Asp Val Ala Ala Leu His Lys
        50                  55                  60

Ala Ile Met Val Lys Gly Val Asp Glu Ala Thr Ile Ile Asp Ile Leu
65                  70                  75                  80

Thr Lys Arg Asn Asn Ala Gln Arg Gln Gln Ile Lys Ala Ala Tyr Leu
                85                  90                  95

Gln Glu Thr Gly Lys Pro Leu Asp Glu Thr Leu Lys Lys Ala Leu Thr
            100                 105                 110

Gly His Leu Glu Glu Val Val Leu Ala Leu Leu Lys Thr Pro Ala Gln
        115                 120                 125

Phe Asp Ala Asp Glu Leu Arg Ala Ala Met Lys Gly Leu Gly Thr Asp
    130                 135                 140

Glu Asp Thr Leu Ile Glu Ile Leu Ala Ser Arg Thr Asn Lys Glu Ile
145                 150                 155                 160

Arg Asp Ile Asn Arg Val Tyr Arg Glu Glu Leu Lys Arg Asp Leu Ala

```
                    165                 170                 175
Lys Asp Ile Thr Ser Asp Thr Ser Gly Asp Phe Arg Asn Ala Leu Leu
                180                 185                 190
Ser Leu Ala Lys Gly Asp Arg Ser Glu Asp Phe Gly
            195                 200
```

<210> SEQ ID NO 12
<211> LENGTH: 115
<212> TYPE: PRT
<213> ORGANISM: Homo sapiens

<400> SEQUENCE: 12

```
Met Ala Met Val Ser Glu Phe Leu Lys Gln Ala Trp Phe Ile Glu Asn
1               5                   10                  15
Glu Glu Gln Glu Tyr Val Gln Thr Val Lys Ser Ser Lys Gly Gly Pro
                20                  25                  30
Gly Ser Ala Val Ser Pro Tyr Pro Thr Phe Asn Pro Ser Ser Asp Val
            35                  40                  45
Ala Ala Leu His Lys Ala Ile Met Val Lys Gly Val Asp Glu Ala Thr
        50                  55                  60
Ile Ile Asp Ile Leu Thr Lys Arg Asn Asn Ala Gln Arg Gln Gln Ile
65                  70                  75                  80
Lys Ala Ala Tyr Leu Gln Glu Thr Gly Lys Pro Leu Asp Glu Thr Leu
                85                  90                  95
Lys Lys Ala Leu Thr Gly His Leu Glu Glu Val Val Leu Ala Leu Leu
                100                 105                 110
Lys Thr Pro
        115
```

<210> SEQ ID NO 13
<211> LENGTH: 321
<212> TYPE: DNA
<213> ORGANISM: Artificial
<220> FEATURE:
<223> OTHER INFORMATION: light chain variable region of VJ-4B6

<400> SEQUENCE: 13

```
aacattgtaa tgacccaatc tcccaaatcc atgtccatgt cagtaggaga gagggtcacc    60
ttgacctgca aggccagtga aaatgtggtt acttatgttt cctggtatca acagaaacca   120
gagcagtctc ctaaactgct gatatacggg gcatccaacc ggtacactgg ggtccccgat   180
cgcttcacag gcagtggatc tgcaacagat ttcactctga ccatcagcag tgtgcaggct   240
gaagaccttg cagattatca ctgtggacag ggttacagct atccgtacac gttcggaggg   300
gggaccaagc tggaaataaa a                                             321
```

<210> SEQ ID NO 14
<211> LENGTH: 321
<212> TYPE: DNA
<213> ORGANISM: Artificial
<220> FEATURE:
<223> OTHER INFORMATION: anti-sense of light chain variable region of
      VJ-4B6

<400> SEQUENCE: 14

```
tttatttcc agcttggtcc ccctccgaa cgtgtacgga tagctgtaac cctgtccaca    60
gtgataatct gcaaggtctt cagcctgcac actgctgatg gtcagagtga aatctgttgc   120
agatccactg cctgtgaagc gatcggggac cccagtgtac cggttggatg ccccgtatat   180
```
cagcagttta ggagactgct ctggtttctg ttgataccag gaaacataag taaccacatt    240
ctcactggcc ttgcaggtca aggtgaccct ctctcctact gacatggaca tggatttggg    300
agattgggtc attacaatgt t                                              321

<210> SEQ ID NO 15
<211> LENGTH: 107
<212> TYPE: PRT
<213> ORGANISM: Artificial
<220> FEATURE:
<223> OTHER INFORMATION: amino acid sequence of the light chain variable
      region of VJ-4B6

<400> SEQUENCE: 15

Asn Ile Val Met Thr Gln Ser Pro Lys Ser Met Ser Met Ser Val Gly
1               5                   10                  15

Glu Arg Val Thr Leu Thr Cys Lys Ala Ser Glu Asn Val Val Thr Tyr
            20                  25                  30

Val Ser Trp Tyr Gln Gln Lys Pro Glu Gln Ser Pro Lys Leu Leu Ile
        35                  40                  45

Tyr Gly Ala Ser Asn Arg Tyr Thr Gly Val Pro Asp Arg Phe Thr Gly
    50                  55                  60

Ser Gly Ser Ala Thr Asp Phe Thr Leu Thr Ile Ser Ser Val Gln Ala
65                  70                  75                  80

Glu Asp Leu Ala Asp Tyr His Cys Gly Gln Gly Tyr Ser Tyr Pro Tyr
                85                  90                  95

Thr Phe Gly Gly Gly Thr Lys Leu Glu Ile Lys
            100                 105

<210> SEQ ID NO 16
<211> LENGTH: 115
<212> TYPE: PRT
<213> ORGANISM: Artificial
<220> FEATURE:
<223> OTHER INFORMATION: amino acid sequence of light chain variable
      region of VJ-4B6

<400> SEQUENCE: 16

Asn Ile Val Met Thr Gln Ser Pro Lys Ser Met Ser Met Ser Val Gly
1               5                   10                  15

Glu Arg Val Thr Leu Thr Cys Lys Ala Ser Glu Asn Val Val Thr Tyr
            20                  25                  30

Val Ser Trp Tyr Gln Gln Lys Pro Glu Gln Ser Pro Lys Leu Leu Ile
        35                  40                  45

Tyr Gly Ala Ser Asn Arg Tyr Thr Gly Val Pro Asp Arg Phe Thr Gly
    50                  55                  60

Ser Gly Ser Ala Thr Asp Phe Thr Leu Thr Ile Ser Ser Val Gln Ala
65                  70                  75                  80

Glu Asp Leu Ala Asp Tyr His Cys Gly Gln Gly Tyr Ser Tyr Pro Tyr
                85                  90                  95

Thr Phe Gly Gly Gly Thr Lys Leu Glu Ile Lys Arg Ala Asp Ala Ala
            100                 105                 110

Pro Thr Val
        115

<210> SEQ ID NO 17
<211> LENGTH: 354
<212> TYPE: DNA
<213> ORGANISM: Artificial
<220> FEATURE:

<223> OTHER INFORMATION: heavy chain variable region of VJ-4B6

<400> SEQUENCE: 17

```
caggtccagc tgcagcagtc tggacctgaa ctggtcaggc ctgggacttc agtgaagatg      60
tcctgcaagg cttctggata caccttcact aactactgga taggttgggc aaagcagagg     120
cctggacatg gccttgagtg gattggagat atttaccctg gaggtgatta ctactaactac   180
aatgagaagt tcaagggcaa ggccacactg actgcagaca atcctccag cacagcctac     240
atgcagttca gcagcctgac atctgaggac tctgccatct attattgtgc aagatggggg    300
ttaggatact actttgacta ctggggccaa ggcatcactc tcacagtctc ctca          354
```

<210> SEQ ID NO 18
<211> LENGTH: 354
<212> TYPE: DNA
<213> ORGANISM: Artificial
<220> FEATURE:
<223> OTHER INFORMATION: anti sense of heavy chain variable region of VJ-4B6

<400> SEQUENCE: 18

```
tgaggagact gtgagagtga tgccttggcc ccagtagtca agtagtatc ctaaccccca      60
tcttgcacaa taatagatgg cagagtcctc agatgtcagg ctgctgaact gcatgtaggc    120
tgtgctggag gatttgtctg cagtcagtgt ggccttgccc ttgaacttct cattgtagtt    180
agtataatca cctccagggt aaatatctcc aatccactca aggccatgtc caggcctctg    240
ctttgcccaa cctatccagt agttagtgaa ggtgtatcca aagccttgc aggacatctt     300
cactgaagtc ccaggcctga ccagttcagg tccagactgc tgcagctgga cctg          354
```

<210> SEQ ID NO 19
<211> LENGTH: 118
<212> TYPE: PRT
<213> ORGANISM: Artificial
<220> FEATURE:
<223> OTHER INFORMATION: amino acid sequence of heavy chain variable region of VJ-4B6

<400> SEQUENCE: 19

```
Gln Val Gln Leu Gln Gln Ser Gly Pro Glu Leu Val Arg Pro Gly Thr
1               5                   10                  15
Ser Val Lys Met Ser Cys Lys Ala Ser Gly Tyr Thr Phe Thr Asn Tyr
            20                  25                  30
Trp Ile Gly Trp Ala Lys Gln Arg Pro Gly His Gly Leu Glu Trp Ile
        35                  40                  45
Gly Asp Ile Tyr Pro Gly Gly Asp Tyr Thr Asn Tyr Asn Glu Lys Phe
    50                  55                  60
Lys Gly Lys Ala Thr Leu Thr Ala Asp Lys Ser Ser Thr Ala Tyr
65                  70                  75                  80
Met Gln Phe Ser Ser Leu Thr Ser Glu Asp Ser Ala Ile Tyr Tyr Cys
            85                  90                  95
Ala Arg Trp Gly Leu Gly Tyr Tyr Phe Asp Tyr Trp Gly Gln Gly Ile
            100                 105                 110
Thr Leu Thr Val Ser Ser
        115
```

<210> SEQ ID NO 20
<211> LENGTH: 123
<212> TYPE: PRT
<213> ORGANISM: Artificial

```
<220> FEATURE:
<223> OTHER INFORMATION: amino acid sequence of heavy chain variable
      region of VJ-4B6

<400> SEQUENCE: 20

Gln Val Gln Leu Gln Gln Ser Gly Pro Glu Leu Val Arg Pro Gly Thr
1               5                   10                  15

Ser Val Lys Met Ser Cys Lys Ala Ser Gly Tyr Thr Phe Thr Asn Tyr
            20                  25                  30

Trp Ile Gly Trp Ala Lys Gln Arg Pro Gly His Gly Leu Glu Trp Ile
        35                  40                  45

Gly Asp Ile Tyr Pro Gly Gly Asp Tyr Thr Asn Tyr Asn Glu Lys Phe
    50                  55                  60

Lys Gly Lys Ala Thr Leu Thr Ala Asp Lys Ser Ser Ser Thr Ala Tyr
65                  70                  75                  80

Met Gln Phe Ser Ser Leu Thr Ser Glu Asp Ser Ala Ile Tyr Tyr Cys
                85                  90                  95

Ala Arg Trp Gly Leu Gly Tyr Tyr Phe Asp Tyr Trp Gly Gln Gly Ile
            100                 105                 110

Thr Leu Thr Val Ser Ser Ala Lys Thr Thr Pro
            115                 120
```